(12) United States Patent
Oh et al.

(10) Patent No.: US 8,916,228 B2
(45) Date of Patent: Dec. 23, 2014

(54) BI-LAYERED BONE-LIKE SCAFFOLDS

(75) Inventors: Daniel Sunho Oh, San Antonio, TX (US); Anson Ong, San Antonio, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 1229 days.

(21) Appl. No.: 12/672,471

(22) PCT Filed: Aug. 8, 2008

(86) PCT No.: PCT/US2008/072686
§ 371 (c)(1),
(2), (4) Date: Sep. 9, 2011

(87) PCT Pub. No.: WO2009/021209
PCT Pub. Date: Feb. 12, 2009

(65) Prior Publication Data
US 2011/0313538 A1     Dec. 22, 2011

Related U.S. Application Data

(60) Provisional application No. 60/955,014, filed on Aug. 9, 2007.

(51) Int. Cl.
*A61L 27/56* (2006.01)
*A61F 2/28* (2006.01)
(Continued)

(52) U.S. Cl.
CPC .............. *A61F 2/30767* (2013.01); *A61F 2/44* (2013.01); *A61F 2002/30968* (2013.01);
(Continued)

(58) Field of Classification Search
USPC .......... 427/2.24, 2.26, 2.27; 623/23.61, 23.58
See application file for complete search history.

(56) References Cited

U.S. PATENT DOCUMENTS 4,629,464 A    12/1986   Takata et al. ................ 623/23.61
4,846,838 A     7/1989   Takai et al. .................... 424/422
(Continued)

FOREIGN PATENT DOCUMENTS

GB         2 317 887          4/1998
WO       WO 02/28322         4/2002

OTHER PUBLICATIONS

Karageorgiou and Kaplan, "Porosity of 3D biomaterial scaffolds and osteogenesis," *Biomaterials*, 26:5474-5491, 2005.

(Continued)

*Primary Examiner* — Cachet Sellman
(74) *Attorney, Agent, or Firm* — Fulbright & Jaworski LLP

(57) ABSTRACT

Biomedical scaffolds are described that may be used, for example, for the treatment of bone diseases and bone reconstruction and restoration. The described scaffolds having ingress and habitiaion property for cells and growth factors with serum by capillary action via engineered micro-channles. Also, the scaffolds permit nutrient and ion flow such that bone regeneration in the area surrounding the scaffold is promoted. Kits that include such scaffolds and methods of preparing and using such scaffolds are also provided.

29 Claims, 39 Drawing Sheets

(51) Int. Cl.
*B05D 3/02* (2006.01)
*A61L 27/42* (2006.01)
*A61F 2/46* (2006.01)
*A61L 27/46* (2006.01)
*A61L 27/12* (2006.01)
*A61F 2/44* (2006.01)
*A61F 2/30* (2006.01)
*A61F 2/08* (2006.01)

(52) U.S. Cl.
CPC ............ *A61F 2002/30062* (2013.01); *A61F 2002/2839* (2013.01); *A61F 2002/2817* (2013.01); *A61F 2/28* (2013.01); *A61F 2002/2871* (2013.01); *A61F 2002/30701* (2013.01); *A61L 27/425* (2013.01); *A61F 2/08* (2013.01); *A61F 2250/0081* (2013.01); *A61F 2/4644* (2013.01); *A61F 2310/00796* (2013.01); *A61F 2002/30957* (2013.01); *A61F 2310/0052* (2013.01); *A61F 2002/30971* (2013.01); *A61F 2002/2892* (2013.01); *A61F 2002/30677* (2013.01); *A61F 2210/0004* (2013.01); *A61F 2/30771* (2013.01); *A61F 2/2875* (2013.01); *A61F 2002/30929* (2013.01); *A61F 2002/30011* (2013.01); *A61F 2002/3092* (2013.01); *A61L 27/46* (2013.01); *A61F 2002/2825* (2013.01); *A61F 2310/00083* (2013.01); *A61F 2250/0023* (2013.01); *A61F 2/30756* (2013.01); *A61F 2002/3024* (2013.01); *A61F 2310/00293* (2013.01); *A61F 2/2803* (2013.01); *A61F 2002/2896* (2013.01); *A61F 2002/307* (2013.01); *A61F 2230/0069* (2013.01); *A61F 2002/30705* (2013.01); *A61L 27/12* (2013.01); *A61F 2310/00473* (2013.01); *A61F 2310/00113* (2013.01); *A61F 2002/30703* (2013.01); *A61L 27/56* (2013.01)
USPC .... 427/2.26; 427/2.24; 427/372.2; 623/23.61

(56) References Cited

U.S. PATENT DOCUMENTS

| | | | |
|---|---|---|---|
| 5,258,044 A | 11/1993 | Lee | 623/66.1 |
| 5,306,305 A | 4/1994 | Lee | 435/325 |
| 5,543,019 A | 8/1996 | Lee et al. | 204/192.15 |
| 5,650,176 A | 7/1997 | Lee et al. | 424/602 |
| 5,676,976 A | 10/1997 | Lee et al. | 424/602 |
| 5,683,461 A | 11/1997 | Lee et al. | 424/423 |
| 5,783,217 A | 7/1998 | Lee et al. | 424/602 |
| 5,843,289 A | 12/1998 | Lee et al. | 204/192.3 |
| 6,027,742 A | 2/2000 | Lee et al. | 424/422 |
| 6,033,582 A | 3/2000 | Lee et al. | 216/37 |
| 6,117,456 A | 9/2000 | Lee et al. | 424/602 |
| 6,132,463 A | 10/2000 | Lee et al. | 600/36 |
| 6,136,369 A | 10/2000 | Leitao et al. | 427/2.27 |
| 6,143,948 A | 11/2000 | Leitao et al. | 424/422 |
| 6,171,610 B1 | 1/2001 | Vacanti et al. | 424/426 |
| 6,214,368 B1 | 4/2001 | Lee et al. | 424/423 |
| 6,302,913 B1 * | 10/2001 | Ripamonti et al. | 623/16.11 |
| 6,309,635 B1 | 10/2001 | Inger et al. | 424/93.7 |
| 6,344,061 B1 | 2/2002 | Leitao et al. | 623/23.5 |
| 6,348,069 B1 | 2/2002 | Vacanti et al. | 623/11.11 |
| 6,479,418 B2 | 11/2002 | Li et al. | 501/81 |
| 2002/0037799 A1 | 3/2002 | Li et al. | 501/82 |
| 2002/0169066 A1 * | 11/2002 | Cassidy et al. | 501/80 |
| 2006/0265081 A1 * | 11/2006 | Turner et al. | 623/23.5 |
| 2006/0292350 A1 | 12/2006 | Kawamura et al. | 428/189 |
| 2008/0069852 A1 | 3/2008 | Shimp et al. | 424/423 |
| 2008/0075675 A1 | 3/2008 | Reynolds | 424/52 |
| 2008/0085292 A1 | 4/2008 | Rezania et al. | 424/422 |
| 2008/0095820 A1 | 4/2008 | Kumta et al. | 424/423 |
| 2008/0097618 A1 | 4/2008 | Baker et al. | 623/23.51 |
| 2008/0103227 A1 | 5/2008 | Yun et al. | 523/105 |

OTHER PUBLICATIONS

Murphy et al., "Salt fusion: an approach to improve pore interconnectivity within tissue engineering scaffolds," *Tissue Engineering*, 8:43-52, 2002.

Search Report and Written Opinion, issued in International Application No. PCT/US2008/072686, mailed Mar. 12, 2009.

* cited by examiner

FIG. 15B

Sponge Surface Treatment

FIG. 15C

Treat with NaOH

FIG. 15I  Fabricate Solid Outside Shell
FIG. 15J  Dissolve CMC
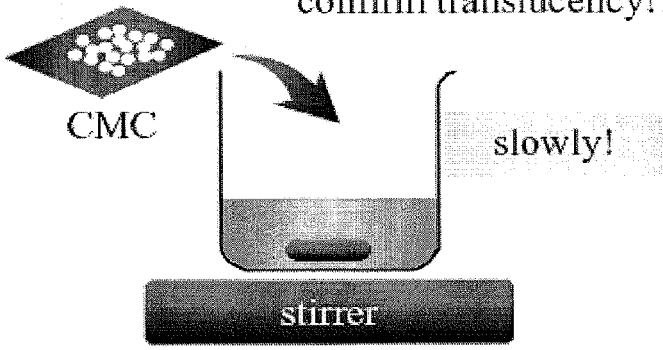
FIG. 15K  Add Sodium Silicate Solution
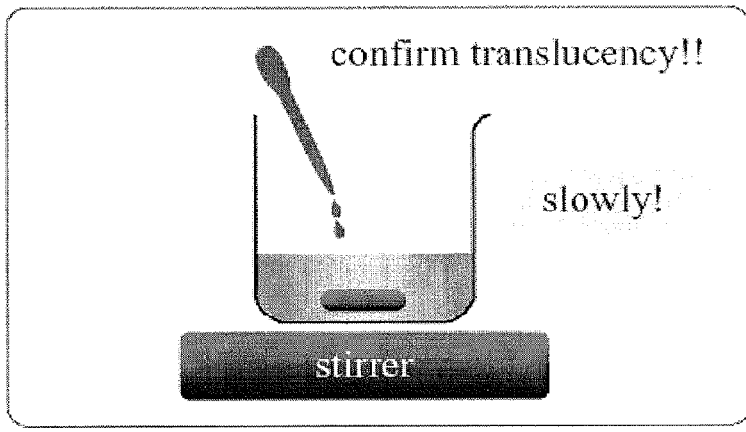

CaP Paste for 1st Coating

Dissolve PVA

Add Sodium Silicate Solution

FIG. 15Z
1st Coating and Sintering
CaP Paste
FIG. 15AA
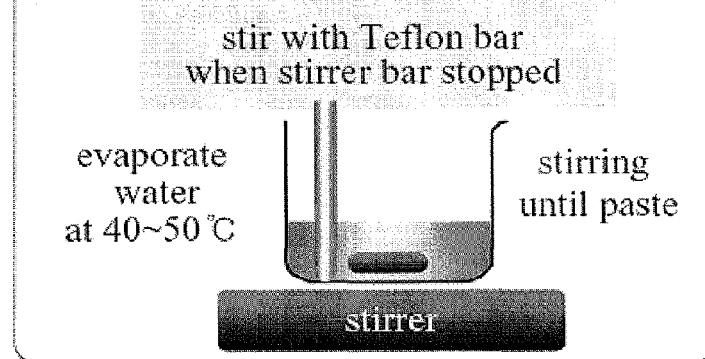
Immerse PU Sponge
FIG. 15BB
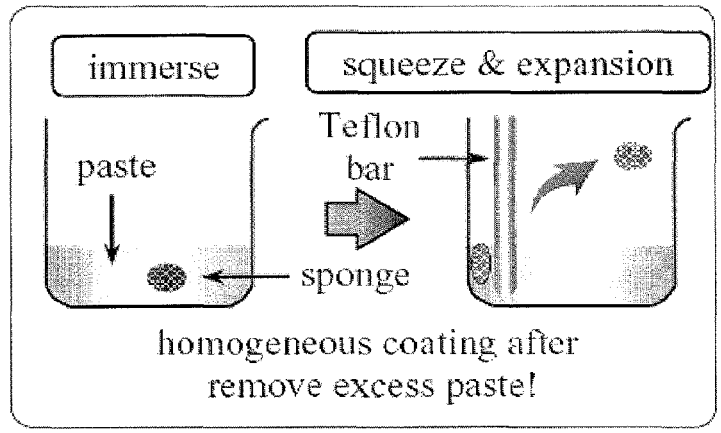

FIG. 15EE
2nd coating CaP Slurry
Dissolve PVA
FIG. 15FF
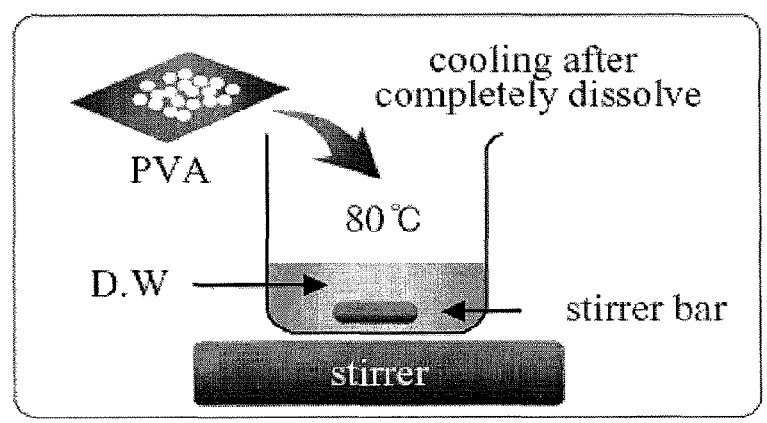
Add Sodium Silicate Solution
FIG. 15GG
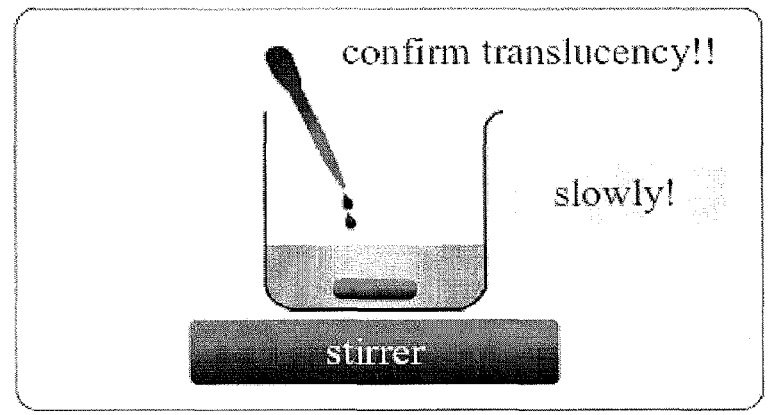

FIG. 15JJ
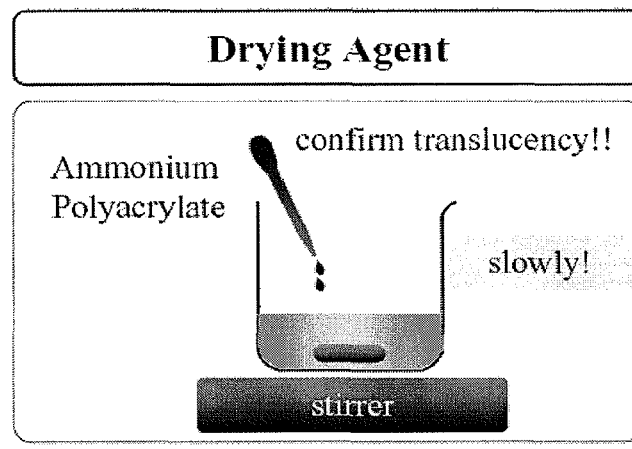
FIG. 15KK
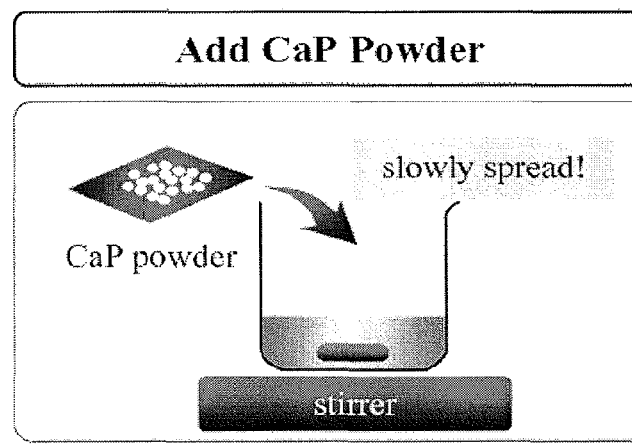
FIG. 15LL
2nd Coating and Sintering
FIG. 15MM
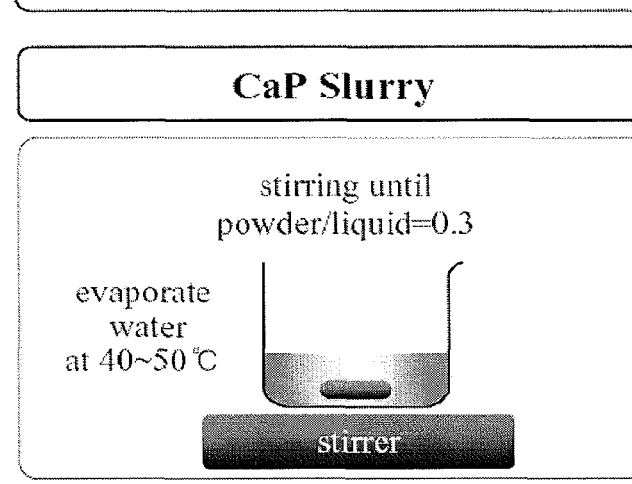

FIG. 15RR — Synthesis Ag Doped CaP-sol by Sol-Gel Method
FIG. 15SS — Prepare Ca, Ag Precursor and P Precursor
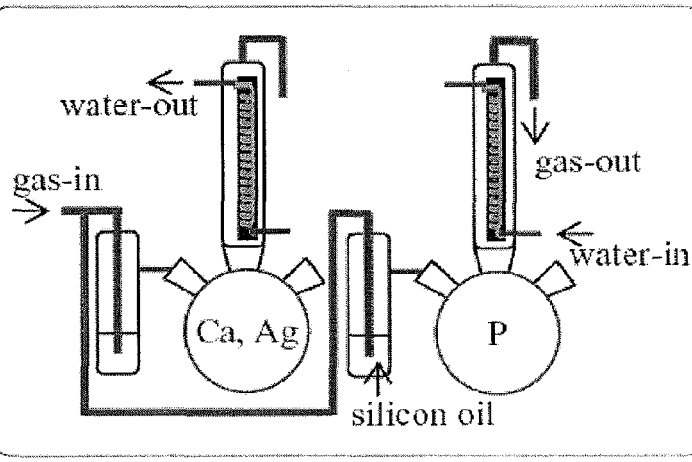
FIG. 15TT — CaP-sol Mixture
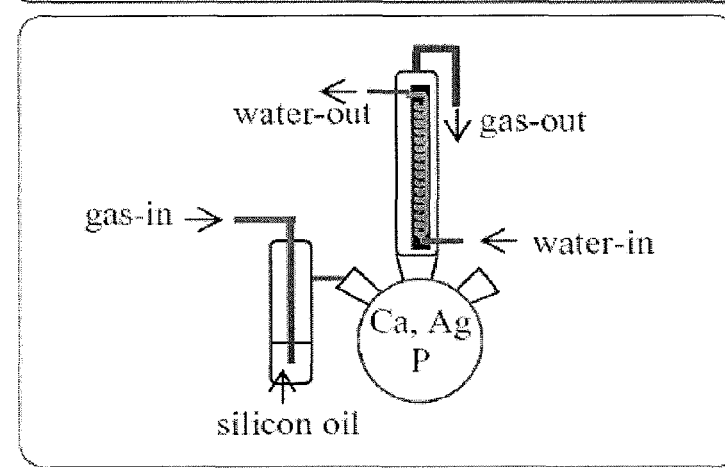

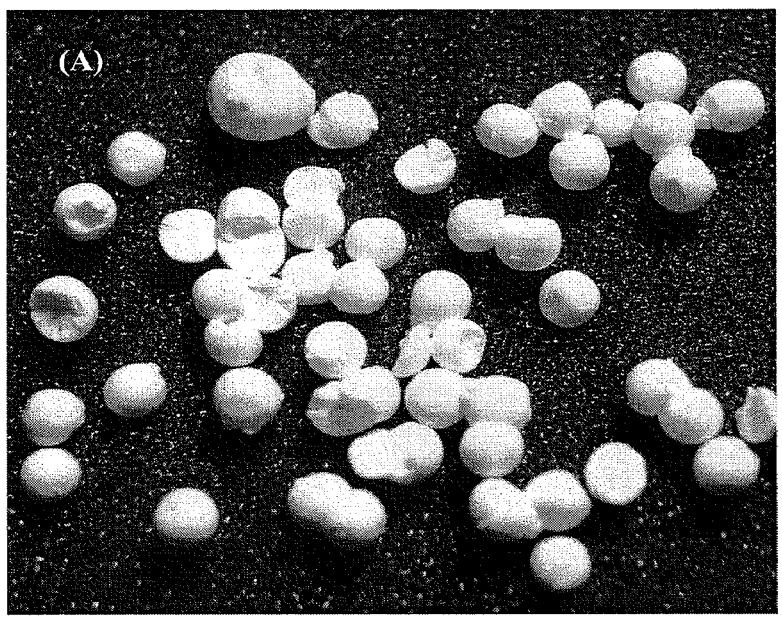
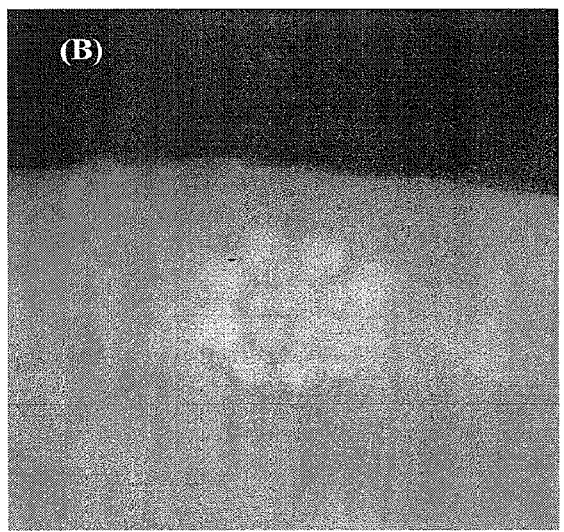
FIGS. 17A-B

BI-LAYERED BONE-LIKE SCAFFOLDS

BACKGROUND OF THE INVENTION

The present application is a national phase application under 35 U.S.C §371 of International Application No. PCT/US2008/072686, filed Aug. 8, 2008, which claims the benefit of priority to U.S. Provisional Patent Application Ser. No. 60/955,014, filed Aug. 9, 2007, the entire contents of each of which are hereby specifically incorporated by reference in their entirety.

1. Field of the Invention

The present invention generally relates to the fields of biomedical scaffolds, and methods of treating disease or disorders in a subject that involve implantation of the scaffolds set forth herein.

2. Description of Related Art

Considerable research has been reported over the last decade in the use of polymeric and ceramic biomaterials for producing scaffolds. However, the ideal material and fabrication technique for optimal bone tissue regeneration has yet to be identified. While current materials and techniques have met with varying successes, each material and/or technique exhibits limitations that must be addressed. In addition, there is an overall lack of success in bringing these technologies to the clinic, especially for the reconstruction and restoration of large bone defects.

Ideally, scaffolds for bone tissue regeneration should 1) exhibit biocompatibility without causing an inflammatory response or foreign body/toxic reaction, 2) have closely matched mechanical properties when compared to native bone, and 3) possess a mechanism to allow diffusion and/or transport of ions, nutrients, and wastes. Strong bonding with the host bone, active bone and vascular in-growth, and biodegradation of the scaffolds (depending on the applications) are equally desirable. Although the use of biodegradable polymer scaffolds has shown some success in terms of beneficial tissue in-growth, there are controversies over their use for bone regenerations. Limitations on the use of polymeric scaffolds have included the presence of hydrophobic surfaces which are not conducive for bone tissue regeneration and the lowering of localized pH during polymeric degradation. Restoration of bone function is also dependent on the closely-matched mechanical properties of the scaffold to the native bone. This mechanical similarity is important as bone is primarily load bearing in function with suitable load transfer necessary to regulate, adapt, and remodel bone during the normal healing process. Additionally, the architecture of the scaffolds (pore size, porosity, interconnectivity and permeability) needed for favorable ion and transport/diffusion of nutrients and wastes is generally perceived as critical for achieving sustained cell proliferation and differentiation within the scaffolds, thereby affecting function and restoration of the regenerated tissue. Although calcium phosphates have been used in the past for scaffold fabrication, different processes or procedures used have often resulted in calcium phosphate scaffolds with different architectures. As such, selection of a manufacturing process becomes important in dictating the scaffold architecture needed for successful bone tissue regeneration.

One example of scaffold architecture and its manufacture is set forth in Kawamura et al., U.S. Publ. Appl. No. 2006/0292350. One limitation of this invention is that it contains no functional interconnecting pore channels for cell migration, ion transport, or waste exchange. This is a limitation of a scaffold discussed by Takata et al., U.S. Pat. No. 4,629,464. Another example of scaffold architecture and its manufacture is set forth by Li et al., U.S. Publ. No. 2002/0037799. This invention is limited at least in part by the provision of only interconnecting pores for cell migration: no other migration means are provided. The scaffolds described by these references and others are limited in the degree of nutrient and ion transport to surrounding tissues. A need exists for the manufacture of scaffolds that better facilitate such transport to improve bone tissue regeneration.

SUMMARY OF THE INVENTION

The present invention is generally directed to new systems and strategies for bone and tissue repair. In particular, the invention generally concerns porous scaffolds which can be applied in the treatment of diseases and prevention of infection in a subject, and methods of making and using these scaffolds. The term "scaffold" is used herein in its broadest sense and is not intended to be limited to any particular shapes, sizes, configurations, or applications. The scaffold can be of any size. For example, it may be at least one cm in length. It refers to any device or material for implantation that aids or augments tissue formation or healing. For example, scaffolds may be applied at a bone defect site, e.g., one resulting from injury, a defect brought about during the course of surgery, infection, malignancy or developmental malformation. Scaffolds of the present invention can be used in a variety of surgical procedures such as the repair of simple fractures, compound fractures, comminuted fractures, and bone non-unions. They may also be used to attach non-bony tissues to bone, such as tendon, cartilage, and synovium. Additional detail regarding therapeutic applications is addressed in the specification below.

In particular embodiments the scaffold of the present invention is a single-density or multi-density porous structure which, upon implantation into a subject, promotes cellular and/or nutrient infiltration from adjacent tissues. The micropores and microchannels can support the in-growth of cell and/or the formation or remodeling of bone.

Particular embodiments of the present invention concern scaffolds having a outer cortical shell and an inner trabecular core. The structure of such scaffolds resembles the structure of a long bone. Such a structure allows the outer cortical shell to be load bearing, as in native bone.

Other embodiments of the present invention concern biomedical scaffolds that include a body having a long axis, wherein the scaffold has an open pore structure of micropores that are interconnected and secondary microchannels which are generally perpendicular to the long axis of the body.

A "micropore" as used herein refers to a small opening or passageway, having an average diameter of about 1 µm to about 3 mm. For example, the micropore may have an average diameter of about 1, 5, 10, 15, 20, 25, 30, 35, 40, 45, 50, 55, 60, 65, 70, 75, 80, 85, 90, 95, 100, 110, 120, 130, 140, 150, 160, 170, 180, 190, 200, 220, 230, 240, 250, 260, 270, 280, 290, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1100, 1200, 1300, 1400, 1500, 1600, 1700, 1800, 1900, 2000, 2100, 2200, 2300, 2400, 2500, 2600, 2700, 2900, or 3000 µm or more, or any range derivable therein. Micropores may or may not be connected to other micropores.

In those embodiments of the present scaffolds that possess interconnected microchannels and/or micropores, all or only a portion of the present scaffolds may possess the microchannels and/or micropores. Microchannels may or may not connect to micropores.

The micropores may be of uniform shape, or may be distinctly shaped. The micropores may be of uniform size, or may be of a variety of sizes. They may be generally round, oval, cyclindrical, or irregularly shaped. A micropore may be interconnected with one or more other micropores or one or more microchannels. In some embodiments the scaffold includes latent pores that become actual pores after the scaffold is implanted in a subject.

A "microchannel" as used herein refers to a passageway that has an average diameter of about 1 µm to about 3 mm, wherein the length of the passageway is at least twice as long as the average diameter of the passageway. For example, the microchannel may have an average diameter of about 1, 5, 10, 15, 20, 25, 30, 35, 40, 45, 50, 55, 60, 65, 70, 75, 80, 85, 90, 95, 100, 110, 120, 130, 140, 150, 160, 170, 180, 190, 200, 220, 230, 240, 250, 260, 270, 280, 290, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1100, 1200, 1300, 1400, 1500, 1600, 1700, 1800, 1900, 2000, 2100, 2200, 2300, 2400, 2500, 2600, 2700, 2900, or 3000 µm or more, or any range derivable therein. The microchannel may have any average length. Length of microchannels may be dependent on size and shape of the scaffold.

A microchannel may be interconnected with one or more other microchannels or with one or more micropores. In embodiments of the present invention that possess an outer cortical shell and an inner trabecular core, the outer cortical shell and/or inner trabecular core may possess one or more microchannels or micropores. Microchannels and/or micropores of the outer cortical layer may be connected to microchannels and/or micropores of the inner travecular core. An interconnected structure of micropores and/or microchannels allows for the transport of nutrients, ions, and/or cells from adjacent tissue following implantation into a subject or on a surface of a subject. In some embodiments, only the outer cortical shell possesses micropores and/or microchannels. In other embodiments, only the inner trabecular core possesses micropores and/or microchannels. In particular embodiments, both the trabecular core and the outer cortical shell possess micropores and/or microchannels.

In certain embodiments, the scaffold is cylindrical in shape and includes an outer cortical shell and inner trabecular layer to resemble the native structure of a portion of a long bone. Some embodiments of such scaffolds possess interconnected secondary microchannels in a radial orientation within struts of the scaffolds in order to provide nutrients and ions to the interior of the structure to facilitate development of weight-bearing support. The "strut" is the main frame of the scaffold structure. The strut may comprise microchannels.

Particular embodiments of the present invention pertain to biomedical scaffolds that include (a) a core component having interconnected micropores; and (b) a cortical layer in contact with at least a portion of a surface of the core component, wherein the cortical layer comprises micropores and/or microchannels. In embodiments of the present invention, the micropores of the core component are interconnected, which allows for the transport of nutrients and ions when implanted in a subject. In further embodiments, the micropores of the cortical layer are interconnected. In still further embodiments, the micropores of the core component are interconnected with the micropores of the cortical layer.

In particular embodiments of the present invention, the micropores of the cortical layer have an average diameter that is less than the average diameter of the micropores of the core component. For example, in some embodiments, the core component is comprised of two populations of micropores, the first population of micropores having an average diameter of about 50 µm to about 1000 µm, and the second population of micropore having an average diameter of about 10 µm to about 300 µm. In more particular embodiments, the first type of micropore has an average diameter of about 150 µm to about 750 µm, and the second type of micropore has an average diameter of about 50 µm to about 120 µm. In particular embodiments, the average diameter of the micropores of the cortical layer is about 1 µm to about 300 µm. In more particular embodiments, the average diameter of the micropores of the cortical layer is about 10 µm to about 150 µm.

The scaffold composite may be of any density. For example, the density may be about 5, 4.5, 4.0, 3.5, 3.0, 2.5, 2.0, 1.9, 1.8, 1.7, 1.6, 1.5, 1.4, 1.3, 1.2, 1.1, 1.0, 0.9, 0.8, 0.7, 0.6, 0.5, 0.4, 0.3, 0.2, or 0.1 g/cm$^3$, or any range of densities derivable therein. In particular embodiments, the density is between about 0.05 g/cm$^3$ and about 1.60 g/g/cm$^3$. In more particular embodiments, the porous composite has a density of between about 0.07 g/cm$^3$ and 1.1 g/cm$^3$. The density may be less than about 1 g/cm$^3$, less than about g/cm$^3$, less than about 0.8 g/cm$^3$, less than about 0.7 g/cm$^3$, less than about 0.6 g/cm$^3$, less than about 0.50 g/cm$^3$, less than about 0.4 g/cm$^3$, less than about 0.3 g/cm$^3$, less than about 0.2 g/cm$^3$, or less than about 0.1 g/cm$^3$.

In embodiments of the present scaffolds that include a porous component, the porous component is of any porosity. For example, the porosity may be at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or more, or any range of porosities derivable herein. The core component and cortical layer of the scaffold can be of any porosity, including any of the porosities set forth above. In particular embodiments, the core component average porosity is 65% to 90% and cortical layer of the scaffold average porosity is 30% to 60%.

The scaffold can be of any shape and configuration. For example, in particular embodiments, the scaffold is cylindrical, thus resembling a long bone. In other embodiments, the scaffold is round, square, or of an irregular shape or comprised of granules of a size smaller than the bony defect they will be used to treat. The granules are generally defined as having an average diameter of less than 1 cm. The scaffold can be fabricated into any shape that is suitable for implantation into a subject. Methods of fabrication of scaffolds are discussed in greater detail below.

In some embodiments, the cortical layer is further defined as comprising microchannels. For example, in scaffolds with a cylindrical shape with a long axis, the secondary microchannels have an axis that is generally perpendicular to the long axis of the scaffold. There can be any number of microchannels in the cortical structure. In some embodiments, the secondary microchannels have an average diameter that is greater than the average diameter of the micropores in the cortical layer. In particular embodiments, the secondary microchannels have an average diameter of about 10 µm to about 500 µm. In more particular embodiments, the secondary microchannels have an average diameter of about 50 µm to about 120 µm.

The core component may include a single population of micropores of uniform size and shape, or may include more than one population of micropores. In some embodiments, the first population of micropores has an average diameter of about 150 µm to about 750 µm, and the second population of micropore having an average diameter of about 50 µm to about 120 µm, wherein the average diameter of the micropores of the cortical layer is about 10 µm to about 150 µm.

The scaffold may be composed of any material, so long as the material, when formed into a scaffold as set forth herein, does not induce any significant toxicity or adverse reaction in the subject. The scaffold may be composed on a single type of material, or more than one material. In scaffolds that include more than one component, such as a scaffold that includes an inner trabecular core and outer cortical layer, the components of the scaffold may be composed on similar materials or different materials. The scaffold may be composed of more than one material, or a composite of materials.

In particular embodiments, the scaffold includes calcium and phosphorus. For example, the calcium phosphate may be tricalcium phosphate, hydroxyapatite, amorphous calcium phosphate, monocalcium phosphate, dicalcium phosphate, octacalcium phosphate, tetracalcium phosphate, fluorapatite, carbonated apatite, an analog thereof, or a mixture thereof. The scaffold may be composed of a composition that includes calcium and phosphate (a calcium phosphate). A "calcium phosphate" as used herein is generally defined as any molecule that includes one or more calcium atoms, one or more phosphorus atoms, and one or more oxygen atoms.

The scaffold may include one or more additional components. Examples include therapeutic agents, such as small molecules, polypeptides, proteins, DNA, RNA, antibodies, antibody fragments, metal ions (such as zinc or silver), and so forth. In particular embodiments the therapeutic agent is an angiogenic factor or an osteogenic growth factor.

In some embodiments, the scaffold may further include particles. The particles in the composite may have a variety of shapes including spheroidal, plate, fiber, cuboidal, sheet, rod, ellipsoidal, string, elongated, polyhedral, and mixtures thereof. The particles in the composite may be of any size. For example, they may have an average size of about 10, 20, 30, 40, 50, 60, 70, 80, 90, 100, 150, 200, 250, 300, 350, 400, 450, 500, 550, 600, 650, 700, 750, 800, 850, 900, or 1000 microns in diameter, or any range of diameter derivable therein. In particular embodiments, the average particle size is about 20 to about 800 microns in diameter. Particles of varying sizes may be present within the same scaffold.

The present invention also generally pertains to methods of treating a bone disease or bone injury in a subject, comprising implanting into the bone of a subject a scaffold as described herein, wherein the bone disease or bone injury is treated. The subject can be any subject, but in particular embodiments is a mammal. For example, the mammal may be a human, a primate, a dog, a sheep, a horse, a goat, a cat, a horse, a cow, a rat, or a mouse. In particular embodiments, the mammal is a human.

In particular embodiments, the subject has a bone fracture or bony defect. The bone fracture or bony defect may be of any cause. For example, the bone fracture or bone defect may be a fracture or defect of a long bone, a weight-bearing bone or a non-weight-bearing bone, such as the tibia, the femur, the radius, the ulna, a vertebrae, the hip, the maxilla, the mandible, the zygomatic bone, or craniofacial bones. The bone disease may be any bone disease, such as fibrous dysplasia, osteoporosis, osteomalacia, arthritis, osteomyelitis, avascular necrosis, Paget's disease, bone cancer, or a traumatic injury. The bone defect may be a defect related to a disease process, to trauma, or to surgical excision of a bone lesion. In some embodiments, the method further includes treating the subject with one or more secondary forms of therapy for treatment of a bone disease or bone fracture.

The scaffold may be fabricated to conform to a shape of a bone or tissue defect, or may be modified by the surgeon at the time of implantation to be of a particular shape or size. In some embodiments, the scaffold is in the form of granules which can be packed into a bony defect by the surgeon.

In some embodiments of the present scaffolds, channels are created in the sides of the scaffolds to create opening into which beads that include one or more therapeutic agents can be placed. The beads can be coated with one or more therapeutic agents, or the therapeutic agents can be incorporated into the structure of the bead. The bead may or may not be resorbable. In particular embodiments, the beads are composed of a polymer, such as any of those polymers set forth herein, or are ceramic. The channels, which may be larger than microchannels as described herein, can be created using any method known to those of ordinary skill in the art. In particular embodiments, the channels are created by drilling into the side of the scaffold.

The present invention also generally pertains to kits that include one or more scaffolds as set forth above in a sealed container. In some embodiments, the kit includes literature in hard copy or electronic format providing information regarding therapeutic application and placement of the scaffold in a subject.

The present invention also generally pertains to methods of making a bone scaffold. For example, in some embodiments the method includes (a) contacting a porous polymer sponge with a composition that includes a suitable material for scaffold formation such as any of those examples set forth above and elsewhere in this specification, wherein at least a portion of the sponge becomes coated with the composition; and (b) drying the composition-coated sponge, wherein a bone scaffold is formed. Examples of materials contemplated include those previously set forth.

As used herein, a "sponge" refers to a porous structure. The sponge may be comprised of any polymer. Examples include polyurethane, polypropylene, polystyrene, an acrylic polymer, a polycarbonate, a polyester, acrylics, polyacrylates, polymethacrylates, fluorocarbons, hydrogels, polyacetals, polyamides, poly(ether, ketones) (PEK), polyimides (nylons), polyolefins, polystyrene, polysulfones, latex, silicone, or a mixture thereof. In particular embodiments, the sponge is comprised of polyurethane.

In particular embodiments, the method further comprises contacting the sponge with about 5% to about 20% sodium hydroxide prior to contacting the sponge with the composition. In more particular embodiments, the method comprises contacting the sponge with about 10% to about 15% sodium hydroxide prior to contacting the sponge with the composition.

The sponge can be of any porosity. In particular embodiments, the sponge has about 10, 15, 20, 25, 30, 35, 40, 45, 50, 55, 60, 65, 70, 75, 80, 85, 90, 95 or 100 pores per inch (ppi), or any range of ppi derivable therein. The pores can be of any size or configuration, including those sizes and configurations set forth above for micropores. In particular embodiments, the sponge has an average porosity of about 40 ppi to about 100 ppi, or about a 40 ppi to about 80 ppi. In some embodiments, the sponge is further defined as having secondary microchannels. The secondary microchannels can be of any size or configuration, examples of which are set forth above.

In some embodiments, the scaffold that is formed includes an inner core and an outer cortical layer. In some embodiments, the core component has an open pore structure of micropores that are interconnected. The cortical layer is in contact with at least a portion of the core component. In some embodiments, the cortical layer includes micropores. In some embodiments, a first sponge is used to fabricate the core component and a second sponge is used to fabricate the cortical layer, and wherein the first sponge and second sponge are each coated with the composition. The first and second sponges may be composed of similar materials or distinct materials. Examples of such materials have been previously set forth.

In some embodiments, the method involves: (a) contacting a core polymer sponge with a composition that includes a composition that includes any of the materials suitable for scaffold material as set forth above, wherein at least a portion of the sponge becomes coated with the composition; and (b) drying the composition-coated sponge, wherein a bone scaffold is formed, may be repeated once, or more than once. In particular embodiments, the composition includes a calcium phosphate.

In particular embodiments, the method further involves sintering the first sponge and second sponge after drying. In some embodiments, the first sponge has an average pore diameter of about 150 μm to about 800 μm after scintering, and the second sponge has an average micropore diameter of about 50 μm to about 250 μm after scintering.

The sponge may be placed in a mold following contacting of the sponge with the composition. In further embodiments, the sponge is placed into a mold prior to contacting the sponge with the composition. The mold allows for shaping of the sponge into a particular desired configuration for therapeutic application. For example, the sponge may be configured to resemble a portion of a bone, such as a long bone. Examples of additional configurations are set forth in the following sections of the specification.

The composition that is contacted with the sponge may include any number of additional components. For example, in some embodiments, the composition includes zinc or silver. The composition may further include a binder. Examples of binders are set forth elsewhere in the specification.

Some or all of the surface of the sponge may be coated with the composition. In particular embodiments, the entire surface of the sponge is coated with the composition. The sponge may be coated or immersed in the composition. Excess composition may be drained or removed from the sponge by other means.

In some embodiments, a first sponge is used to form an inner core of the scaffold, and a second sponge is used to form a cortical layer of the scaffold. The sponge can be of any size, shape, or configuration, as discussed above in the section of the summary pertaining to scaffolds of the present invention. Additionally, channels can be created, such as by drilling or piercing the cortical layer or the trabecular inner core of the scaffold with a piercing element, or incorporating material into the scaffold which provides for pore formation.

In a further embodiment of the invention a biologically active substance is integrated into the scaffold and/or into a coating applied to the scaffold, or coating the inner aspect of the micropores of the scaffold. Thus, a controlled delivery of the biologically active substance is enabled. The amount of the biologically active substance may easily be defined by controlling the coating process, for example. By integrating biologically active substance into a submerged coating layer or region, or into the composition, a controlled retarded release of the biologically active substance may be accomplished. The biologically active substance can also be encapsulated in biodegradable microspheres or polymeric scaffolds and incorporated into channels of the scaffold using any method known to those of ordinary skill in the art, or incorporated into a particle.

It is specifically contemplated that any limitation discussed with respect to one embodiment of the invention may apply to any other embodiment of the invention. Furthermore, any composition of the invention may be used in any method of the invention, and any method of the invention may be used to produce or to utilize any composition of the invention.

The use of the term "or" in the claims is used to mean "and/or" unless explicitly indicated to refer to alternatives only or the alternative are mutually exclusive, although the disclosure supports a definition that refers to only alternatives and "and/or."

Throughout this application, the term "about" is used to indicate that a value includes the standard deviation of error for the device and/or method being employed to determine the value.

As used herein the specification, "a" or "an" may mean one or more, unless clearly indicated otherwise. As used herein in the claim(s), when used in conjunction with the word "comprising," the words "a" or "an" may mean one or more than one. As used herein "another" may mean at least a second or more.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

The following figures form part of the present specification and are included to further demonstrate certain aspects of the present invention. The invention may be better understood by reference to one or more of these drawings in combination with the detailed description of specific embodiments presented herein.

FIG. 1A shows the longitudinal cross section of a bi-layered scaffold with the porous outer cortical shell (1) and porous inner trabecular core structure (2). FIG. 1B shows cross-section of a bi-layered scaffold with the porous outer cortical shell (1) and porous inner trabecular core structure (2). FIG. 1C shows the cross-section of a dense calcium phosphate-coated strut (3) with the presence of triangular secondary microchannel (4) within the strut.

(FIG. 14B)—inner layer of strut; (FIG. 14C)—roughed surface of strut; and (FIG. 14D)—cross section of the hollow strut.

FIG. 15A. Polyurethane (PU) sponges may be used to produce interconnected porous CaP scaffolds. FIG. 15AA. After adding the calcium phosphate, powder further stirring is conducted and the slurry is heated at 40-50° C. for water evaporation during stirring until the powder/liquid ratio is 1.0-1.25. If stirrer bar is stopped during stirring, stir with a Teflon bar until to get the desired powder/liquid ratio. FIG. 15CC-DD. After examining the homogeneous coating, the pre-formed scaffold is dried at 30° C., 50-70% humidity. Then the pre-dried calcium phosphate coated mono or bi-layered pre-formed scaffold is dried at 25° C., under 30% humidity air conditions, for 6-24 hours depending on the pre-formed size. After completely driying, the pre-formed scaffold is put into a furnace for 1st sintering. FIG. 15FF-KK. See comments of FIG. 15T-Y. FIG. 15MM. After adding the calcium phosphate powder, further stirring is conducted and the slurry is heated at 40-50° C. for water evaporation during stirring until powder/liquid ratio is 0.3-0.4. FIG. 15NN. The 1st sintered mono or bi-layered scaffold is immersed in the calcium phosphate slurry and taken out after 5 seconds. Excess slurry is removed using air to avoid filling the primary pores with slurry. FIG. 15OO. The 2nd time coated mono or bi-layered scaffold is centrifuged to remove the 2nd excess slurry and to obtain a homogeneous coating for 10-20 seconds at 1000-2000 rpm, depending on scaffold size and slurry viscosity. FIG. 15PP-QQ. After centrifuging, the scaffold is dried at 25° C., under 30% humidity air conditions, for 6-24 hours depending on the pre-formed size. After completely drying the 2nd time coated scaffold, it is placed into a furnace for 2nd sintering. FIG. 15RR. Antibacterial calcium phosphate doped with silver or zinc can be synthesized using the Sol-Gel method. FIG. 15TT. The silver- or zinc-doped calcium phosphate sol is then synthesized by reacting calcium and phosphorus precursors for a period of 1 to 2 hours and with vigorous stirring. The reaction is performed under an argon atmosphere. FIG. 15UU. The synthesized silver- or zinc-doped calcium phosphate sol is then filtrated through a 0.20 µm to 0.45 µm syringe filter, followed by aging at temperatures ranging from 40° C. to 80° C. and for a period ranging from 12 to 204 hours. FIG. 15VV. The fabricated porous calcium phosphate scaffolds are then immersed in the aged calcium phosphate sol doped with or without silver or zinc. After immersing for 5 to 10 seconds, the scaffold is then removed from the sol and air blown to unclog the pores. FIG. 15WW. The scaffolds are centrifuged to remove excess sol. FIG. 15XX. The calcium phosphate sol coated scaffold is then baked and dried in an oven at temperatures ranging from 50° C. to 100° C. and for a period ranging from 3 to 8 hours. After they are completely dried, the calcium phosphate sol-coated scaffolds are then heat-treated at temperatures ranging from 600° C. to 700° C. using a muffle furnace in air for a period ranging from 1 hour to 5 hours.

FIGS. 17A-B. Granules of the present invention. FIG. 17B—imaging of granules following placement in bony defect.

DESCRIPTION OF ILLUSTRATIVE EMBODIMENTS

Figure 1:
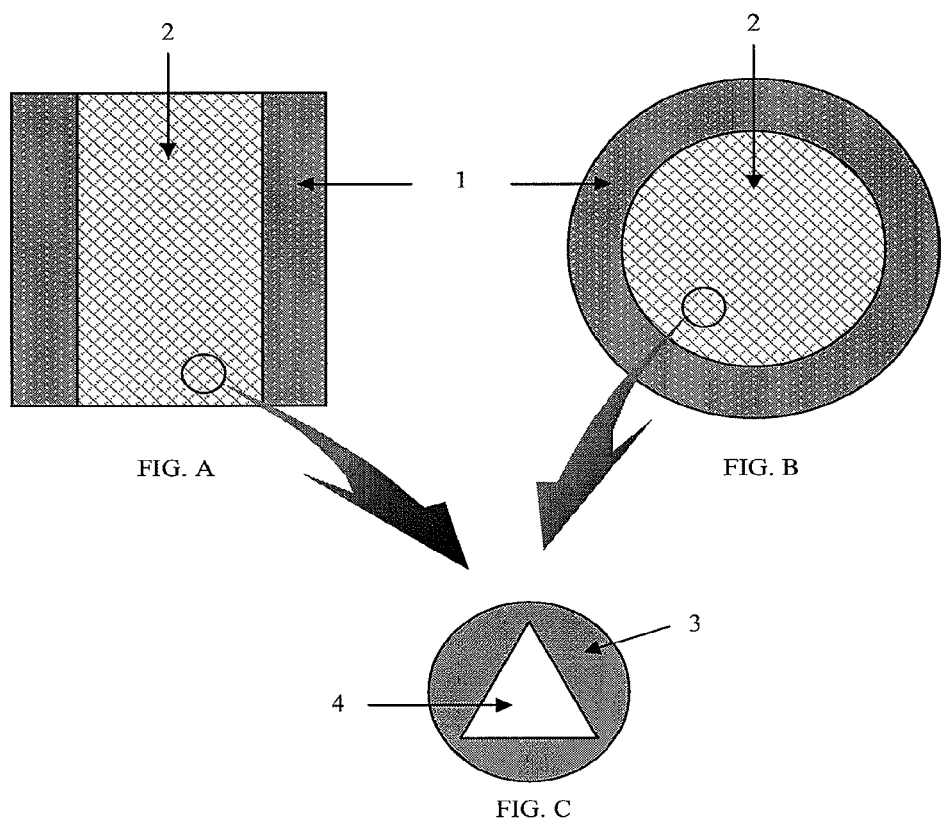
FIGS. 1A-C. Schematic illustrating an example of a bi-layered and multi structural bone-like three-dimensional calcium phosphate scaffold for bone augmentation.

The present invention is based on the development of scaffolds for bone and tissue repair that permit facile transport of nutrients and ions from the surrounding environment into the scaffold, thereby promoting restoration of tissue structure and function.

A. Scaffold Components

The scaffolds of the present invention may be composed of a variety of components. The components can be obtained from natural sources, commercial sources, or can be chemically synthesized. In particular embodiments, the scaffold includes a calcium phosphate. Regarding natural sources, calcium phosphates are found in bone, teeth and shells of a large variety of animals. It exists in a variety of forms known in the art, and non-limiting examples include hydroxyapatite (Hydroxyapatite, $Ca_{10}(PO_4)_6(OH)_2$, $Ca/P=1.67$), tricalcium phosphate (TCP, $Ca_3(PO_4)_2$, $Ca/P=1.5$) and brushite ($CaHPO_4.2H_2O$, $Ca/P=1$. Hydroxyapatite has characteristics similar to mineralized matrix of natural bone, and is biocompatible. Non-limiting examples of calcium compounds include calcium nitrate tetrahydrate, calcium nitrate, and calcium chloride. Non-limiting examples of phosphorus compounds include triethylphosphate, sodium phosphate, and ammonium phosphate dibasic. One of ordinary skill in the art would be familiar with the wide variety of calcium phosphates known in the art, and sources of such compounds.

There are several reported methods for the synthesis of hydroxyapatite. Processes include aqueous colloidal precipitation, sol-gel, solid-state and mechano-chemical methods. Information regarding stabilized calcium phosphate complexes can be found in U.S. Patent App. Pub. No. 20080075675, herein specifically incorporated by reference. Additional information regarding synthesis of hydroxyapatite can be found in U.S. Patent App. Pub. No. 20080095820 and U.S. Pat. No. 6,171,610, herein specifically incorporated by reference in their entirety.

This method includes reacting calcium and a non-acidic ionic phosphate, such as trisodium phosphate, in the presence of hydroxyl ions. U.S. Pat. Nos. 5,258,044, 5,306,305, 5,543, 019, 5,650,176, 5,676,976, 5,683,461, 5,783,217, 5,843,289, 6,027,742, 6,033,582, 6,117,456, 6,132,463 and 6,214,368 disclose methods of synthesizing calcium phosphate particles and a variety of biomedical uses, and are incorporated herein by reference in their entirety.

The scaffolds of the present invention may include any component known to those of ordinary skill in the art to be suitable for inclusion in a biomedical scaffold. Other non-limiting examples of such components include polymethylmethacrylate (PMMA), calcium sulfate compounds, calcium aluminate compounds, aluminum silicate compounds, bioceramic materials, or polymers. Examples of the bioceramic material include calcium phosphate-based oxide, such as apatite, BIOGLASS.™., glass oxide, titania, zirconia, and alumina. Other suitable materials include alginate, chitosan, coral, agarose, fibrin, collagen, bone, silicone, cartilage, aragonite, dahlite, calcite, amorphous calcium carbonate, vaterite, weddellite, whewellite, struvite, urate, ferrihydrite, francolite, monohydrocalcite, magnetite, goethite, dentin, calcium carbonate, calcium sulfate, calcium phosphosilicate, sodium phosphate, calcium aluminate, a-tricalcium phosphate, a dicalcium phosphate, β-tricalcium phosphate, tetracalcium phosphate, octacalcium phosphate (OCP), fluoroapatite, chloroapatite, magnesium-substituted tricalcium phosphate, carbonate hydroxyapatite, and combinations and derivative thereof. Examples of silicon compounds include tetraethylorthosilicate, 3-mercaptopropyltrimethoxysilane, and 5,6-epoxyhexyltriethoxysilane.

The scaffolds of the present invention may optionally include any number of additional additives. In some embodiments, additives are added to a portion of the scaffold. For example, a scaffold may include additives in the cortical shell but not in the inner trabecular core, or vice versa. In some embodiments, there are additives in both the cortical shell and trabecular core. Non-limiting examples of additives include radiocontrast media to aid in visualizing the scaffold with imaging equipment. Examples of radiocontrast materials include barium sulfate, tungsten, tantalum, or titanium. Additives that include osteoinductive materials may be added to promote bone growth into the hardened bone augmentation material. Suitable osteoinductive materials may include proteins from transforming growth factor (TGF) beta superfamily, or bone-morphogenic proteins, such as BMP2 or BMP7.

In preferred embodiments of the present invention the scaffolds set forth herein are biocompatible. The term "biocompatible" is intended to describe any material which upon implantation does not elicit a substantial detrimental response in vivo.

In particular embodiments of the present invention, the scaffold is biodegradable, bioerodible, or resorbable, unless a permanent matrix is desired. The terms "biodegradable", "bioerodable" and "resorbable" arc used herein interchangeably. When used to characterize materials, they refer to materials that degrade under physiological conditions to form a product that can be metabolized or excreted without damage to the subject. In certain embodiments, the product is metabolized or excreted without permanent damage to the subject. Biodegradable materials may be hydrolytically degradable, may require cellular and/or enzymatic action to fully degrade, or both. Other degradation mechanisms, e.g., thermal degradation due to body heat, are also envisioned. Biodegradable materials also include materials that are broken down within cells. Degradation may occur by hydrolysis, enzymatic processes, phagocytosis, or other processes.

Either natural or synthetic polymers can be used to form the scaffold matrix. U.S. Pat. Nos. 6,171,610, 6,309,635 and 6,348,069, which are incorporated herein by reference for their teachings regarding the art of tissue engineering, disclose a variety of matrices for use in tissue engineering.

In some embodiments which include an outer cortex and an inner core, only the outer cortex is biodegradable. In further embodiments, only the inner core is biodegradable. Non-limiting examples of synthetic polymers suitable for inclusion in the scaffolds of the present invention include fibrin, collagen, glycosaminoglycans (GAGs), such as chitin, chitosan and hyaluronic acid, polysaccharides, such as starch, carrageenan, alginate, heparin, glycogen and cellulose, polylactide (PLA), polylactide-co-glycolide (PLGA), polyglycolic acid (PGA), polyurethanes, polycaprolactone, polymethyl methacrylate (PMMA), polyamino acids, such as poly-L-lysine, polyethyleneimine, poly-anhydrides, polypropylene-fumarate, polycarbonates, polyamides, polyanhydrides, polyortho esters, polyacetals, polycyanoacrylates and degradable polyurethanes.

Useful non-erodible polymers include without limitation, polyacrylates, ethylene-vinyl acetate polymers and other acyl substituted cellulose acetates and derivatives thereof, non-erodible polyurethanes, polystyrenes, polyvinyl chloride, polyvinyl fluoride, poly(vinyl imidazole), chlorosulphonated polyolifins, polyethylene oxide, polyvinyl alcohol, TEFLON.™., nylon, stainless steel, cobalt chrome, titanium and titanium alloys, and bioinert ceramic particles (e.g., alumina and zirconia particles), polyethylene, polyvinylacetate, polymethylmethacrylate, silicone, polyethylene oxide, polyethylene glycol, polyurethanes, and natural biopolymers (e.g., cellulose particles, chitin, keratin, silk, and collagen particles), and fluorinated polymers and copolymers (e.g., polyvinylidene fluoride).

In some embodiments, the scaffold is coated with compounds to facilitate attachment of cells to the scaffold. Examples of such compounds include basement membrane components, agar, agarosc, gelatin, gum arabic, collagens types I, II, III, IV, and V, fibronectin, laminin, glycosaminoglycans, polyvinyl alcohol, and mixtures thereof.

In some embodiments, mammalian cells are incorporated into the scaffolds. Information regarding incorporation of mammalian cells can be found in U.S. Pat. App. 20080085292, herein specifically incorporated by reference. For example, mammalian cells may be seeded or cultured with the scaffolds of the present invention prior to implantation in a subject. Examples of such cells include, but are not limited to, bone marrow cells, smooth muscle cells, stromal cells, stem cells, mesenchymal stem cells, synovial derived stem cells, embryonic stem cells, umbilical cord blood cells, umbilical Wharton's jelly cells, blood vessel cells, chondrocytes, osteoblasts, osteoclasts, precursor cells derived from adipose tissue, bone marrow derived progenitor cells, kidney cells, intestinal cells, islets, beta cells, pancreatic ductal progenitor cells, Sertoli cells, peripheral blood progenitor cells, fibroblasts, glomus cells, keratinocytes, nucleus pulposus cells, annulus fibrosus cells, fibrochondrocytes, stem cells isolated from adult tissue, oval cells, neuronal stem cells, glial cells, macrophages and genetically transformed cells or combination of the above cells. The cells can be seeded on the scaffolds for a short period of time just prior to implantation (such as one hour, six hours, 24 hours), or cultured for longer periods of time (such as 2 days, 3 days, 5 days, 1 week, 2 weeks) to promote cell proliferation and attachment within the scaffold prior to implantation.

B. Fabrication of Scaffolds

1. Formation of Pores and Microchannels

Formation of pores and microchannels in the scaffolds set forth herein may be accomplished using any method known to those of ordinary skill in the art. In some embodiments, as discussed in the Example section below, micropores and microchannels are created in a scaffold using a template, such as a sponge. A composition, such as a calcium phosphate, is then applied to the template. For example, in some embodiments the method includes (a) contacting a porous polymer sponge with a composition that includes a suitable material for scaffold formation, wherein at least a portion of the sponge becomes coated with the composition; and (b) drying the composition-coated sponge, wherein a bone scaffold is formed. In some embodiments, the sponge is burned out of the scaffold.

Other methods of creating micropores or microchannels that may be applied in the context of the present invention include, but are not limited to, leaching processes, gas foaming processing, supercritical carbon dioxide processing, sintering, phase transformation, freeze-drying, cross-linking, molding, porogen melting, polymerization, melt-blowing, and salt fusion (reviewed in Murphy et al., 2002; Karageorgiou et al., 2005). Porosity may be a feature of the composition during manufacture or before implantation, or the porosity may only be available after implantation. Additional information regarding formation of pores in a scaffold can be found in U.S. Patent App. Pub. No. 20080069852, herein specifically incorporated by reference. In some embodiments, microchannels and/or larger channels are drilled into the scaffold following molding.

The present invention also contemplates applications using porogens to create latent pores in a composite. These latent pores may arise from including porogens in the composite. The porogen may be any chemical compound that will reserve a space within the composite while the composite is being molded and will diffuse, dissolve, and/or degrade prior to or after implantation leaving a pore in the composite. Porogens may be of any shape or size, such as spheroidal, cuboidal, rectangular, elonganted, tubular, fibrous, disc-shaped, platelet-shaped, or polygonal. In certain embodiments, the porogen is granular. The porogen may be a gas, liquid, or solid. Exemplary gases that may act as porogens include carbon dioxide, nitrogen, argon, or air. Exemplary liquids include water, organic solvents, or biological fluids (such as blood, lymph, plasma). Examples of possible solid porogens include water soluble compounds such as carbohydrates (e.g., sorbitol, dextran poly(dextrose), starch), salts, sugar alcohols, natural polymers, synthetic polymers, and small molecules.

Additional information regarding incorporation of pores into a material can be found in U.S. Patent App. Pub. No. 20080103227, herein specifically incorporated by reference.

2. Shaping

Figure 16:
FIG. 16. Curved custom made scaffold to fit the shape, anatomical structure and size of rabbit tibia.

The scaffolds set forth herein can be formed into a desired shape using any method known to those of ordinary skill in the art. For example, the scaffold may be molded into a desired shape or fractured into granules. The granules retain the essential micropores and/or microchannels. The scaffold may be configured by the surgeon prior to implantation or at the time of implantation into a desired shape, such as a curved custom made scaffold to fit the shape, anatomical structure and size of tibia shown as FIG. 16. In some embodiments, a scaffold of the present invention is fractured into granules which in turn can be packed into a bony defect by the surgeon. The granules may be of a uniform size, or of varying sizes.

3. Formation of Cortex and Coatings

Certain embodiments of the present scaffolds include an outer cortex or coating. Formation of an outer cortex or coating on a core component can be performed using any method known to those of ordinary skill in the art. As discussed in the Examples below, a template (such as a sponge) may be applied in forming an outer cortex on a scaffold. U.S. Patent App. Pub. No. 20080097618, herein specifically incorporated by reference, provides information regarding deposition of calcium phosphate coatings on surfaces. In some embodiments, forming a coating involves dipping or immersing a scaffold in a composition or a plasma spray deposition process. Information concerning immersion techniques can be found in U.S. Pat. Nos. 6,143,948, 6,136,369 and 6,344,061, herein incorporated by reference in their entirety.

C. Therapeutic Applications

Accordingly, methods and scaffolds of the present invention may also be used to treat, or prevent, a bone disease, bone disorder, or bone injury (e.g., a bone fracture). "Treatment" and "treating" as used herein refer to administration or application of a therapeutic agent to a subject or performance of a procedure or modality on a subject for the purpose of obtaining a therapeutic benefit of a disease or health-related condition.

The term "therapeutic benefit" or "therapeutically effective" as used throughout this application refers to anything that promotes or enhances the well-being of the subject with respect to the medical treatment of a condition. This includes, but is not limited to, a reduction in the frequency or severity of the signs or symptoms of a disease.

"Prevention" and "preventing" are used according to their ordinary and plain meaning to mean "acting before" or such an act. In the context of a particular disease or health-related condition, those terms refer to administration or application of an agent, drug, or remedy to a subject or performance of a procedure or modality on a subject for the purpose of blocking the onset of a disease or health-related condition. For example, a scaffold of the present invention may be used to prevent bone disease in a subject. The scaffolds of the present invention may, in certain embodiments, be utilized as an implant for a therapeutic benefit. In particular embodiments, the implants are used for bone augmentation, such as in large defects. In certain embodiments, the scaffolds of the present invention are shaped to duplicate bone lost by a subject, such as a subject who has lost bone matter due to, e.g., an accident, war, gunshot, or surgery. Scaffolds shaped in this matter, may, for example, be implanted in the subject such that the body may regenerate bone tissues to replace the lost matter.

Therapeutic agents may be added to the scaffolds or incorporated into the scaffolds of the present invention using any method known to those of ordinary skill in the art. A "therapeutic agent" as used herein refers to any agent that can be applied in the diagnosis, treatment, or prevention of a disease or health-related condition in a subject. Therapeutic agents include biomolecules. The term "biomolecules", as used herein, refers to the class of molecules (e.g., proteins, amino acids, peptides, polynucleotides, nucleotides, carbohydrates, sugars, lipids, glycoproteins, nucleoproteins, lipoproteins, steroids, etc.) that are commonly found in cells or tissues, whether the molecules themselves are naturally-occurring or artificially created (e.g., by synthetic or recombinant methods). For example, biomolecules include, but are not limited to, enzymes, receptors, neurotransmitters, hormones, cytokines, cell response modifiers such as growth factors and chemotactic factors, antibodies, vaccines, haptens, toxins, interferons, ribozymes, anti-sense agents, plasmids, DNA, and RNA.

Thus, the therapeutic agent may be any agent known to those of ordinary skill in the art. One or more therapeutic agents may be coated on the surface of the scaffold, incorporated into the matrix, incorporated into microspheres which are suspended and distributed in the matrix, or the scaffold can be immersed in a composition comprising one or more agents prior to implantation in a subject.

Examples of classes of therapeutic agents include osteogenic, osteoinductive, and osteoconductive agents, anti-cancer substances, antibiotics, anti-inflammatory agents, immunosuppressants, anti-viral agents (including anti-HIV agents), enzyme inhibitors, neurotoxins, opioids, hypnotics, antihistamines, lubricants, tranquilizers, anti-convulsants, muscle relaxants, anti-Parkinson agents, antispasmodics, antibiotics, antiviral agents, antifungal agents, modulators of cell-extracellular matrix interactions including cell growth inhibitors and anti-adhesion molecules, vasodilating agents, inhibitors of DNA, RNA, or protein synthesis, antiypertensives, analgesics, anti-pyretics, steroidal and non-steroidal anti-inflammatory agents, anti-angiogenic factors, angiogenic factors, anti-secretory factors, anticoagulants and/or antithrombotic agents, local anesthetics, prostaglandins, targeting agents, chemotactic factors, receptors, neurotransmitters, proteins, cell response modifiers, cells, peptides, polynucleotides, viruses, vaccines, amino acid, peptide, protein, glycoprotein, lipoprotein, antibody, steroidal compound, antibiotic, antimycotic, cytokine, vitamin, carbohydrate, lipid, extracellular matrix, extracellular matrix component, chemotherapeutic agent, cytotoxic agent, growth factor, anti-rejection agent, analgesic, anti-inflammatory agent, viral vector, protein synthesis co-factor, hormone, endocrine tissue, synthesizer, enzyme, polymer-cell scaffolding agent with parenchymal cells, angiogenic drug, collagen lattice, antigenic agent, cytoskeletal agent, mesenchymal stem cells, bone digester, antitumor agent, cellular attractant, fibronectin, growth hormone cellular attachment agent, immunosuppressant, nucleic acid, surface active agent, hydroxyapatite, and penetration enhancer, anti-inflammatory agents, growth factors, angiogenic factors, antibiotics, analgesics, chemotactic factors, bone morphogenic protein, and cytokines In particular embodiments the therapeutic agent is an agent that promotes wound healing or prevent infection. Non-limiting examples of such agents include antibiotics, anti-inflammatory drugs, or analgesics.

Non-limiting examples of therapeutic agents include non-collagenous proteins such as osteopontin, osteonectin, bone sialo proteins, fibronectin, laminin, fibrinogen, vitronectin, trombospondin, proteoglycans, decorin, proteoglycans, beta-glycan, biglycan, aggrecan, veriscan, tanascin, matrix gla protein hyaluran, cells; amino acids; peptides; inorganic elements; inorganic compounds; organometallic compounds; cofactors for protein synthesis; cofactors for enzymes; vitamins; hormones; soluble and insoluble components of the immune system; soluble and insoluble receptors including truncated forms; soluble, insoluble, and cell surface bound ligands including truncated forms; chemokines, interleukines; antigens; bioactive compounds that are endocytozed; tissue or tissue fragments; endocrine tissue; enzymes such as collagenase, peptidases, oxidases, etc; polymeric cell scaffolds with parenchymal cells; angiogenic drugs, polymeric carriers containing bioactive agents; encapsulated bioactive agents; bioactive agents in time-release form; collagen lattices, antigenic agents; cytoskeletal agents; cartilage fragments; living cells such as chondrocytes, osteoblasts, osteoclasts, fibroclasts, bone marrow cells, mesenchymal stem cells, etc; tissue transplants; bioadhesives; bone morphogenic proteins (BMPs), transforming growth factors (TGF-.beta.), insulin-like growth factor, platelet derived growth factor (PDGF); fibroblast growth factors (FGF), vascular endothelial growth factors (VEGF), epidermal growth factor (EGF), growth factor binding proteins, e.g., insulin-like growth factors; angiogenic agents;

bone promoters; cytokines; interleukins; genetic material; genes encoding bone promoting action; cells containing genes encoding bone promoting action; cells genetically altered by the hand of man; externally expanded autograft or xenograft cells; growth hormones such as somatotropin; bone digestors; anti-tumor agents; fibronectin; cellular attractants and attachment agents; immunosuppressants; bone resorption inhibitors and stimulators; mitogenic factors; bioactive factors that inhibit and stimulate second messenger molecules; cell adhesion molecules, e.g., cell-matrix and cell-cell adhesion molecules; secondary messengers; monoclonal antibodies specific to cell surface determinants on mesenchymal stem cells; portions of monoclonal antibodies specific to cell surface determinants on mesenchymal stem cells; portions of monoclonal antibodies specific to cell surface determinants on mesenchymal stem cells; clotting factors; polynucleotides; and combinations thereof.

The amount of therapeutic agent included in scaffold can vary widely and will depend on such factors as the agent being delivered, the site of administration, the patient's physiological condition, etc. The optimum levels will be determined in a specific case based upon the intended use of the implant.

In some embodiments, a therapeutic nucleic acid is incorporated into the scaffold. Information regarding incorporation of a therapeutic nucleic acid into scaffolds can be found in U.S. Patent App. Pub. No. 20080095820, herein specifically incorporated by reference. Thus, the scaffolds set forth herein can be applied as gene delivery vehicles.

The scaffolds of the present invention may be used in many applications. Non-limiting examples of such applications include the repair of defects or degeneration of bone, cartilage, tendons, and ligaments. The scaffolds set forth herein can have therapeutic application in other organs of the body as well.

The scaffolds of the present invention can have any desired shape, and the selection of such shape will depend largely on the application of the scaffold. Non-limiting examples of such shapes include cylinder, block, morsel, wedge, and sheet.

In particular embodiments the scaffold will be cylinder shaped for application in the repair of bony defects of long bones. In some embodiments, the scaffold is configured for the repair of a simple fracture, compound fracture or non-union; as an external fixation device or internal fixation device; for joint reconstruction, arthrodesis, arthroplasty or cup arthroplasty of the hip; for femoral or humeral head replacement; for femoral head surface replacement or total joint replacement; for repair of the vertebral column, spinal fusion or internal vertebral fixation; for tumor surgery; for deficit filling; for discectomy; for laminectomy; for excision of spinal tumors; for an anterior cervical or thoracic operation; for the repairs of a spinal injury; for scoliosis, for lordosis or kyphosis treatment; for intermaxillary fixation of a fracture; for mentoplasty; for temporomandibular joint replacement; for alveolar ridge augmentation and reconstruction; as an inlay osteoimplant; for implant placement and revision; for sinus lift; for a cosmetic procedure; and, for the repair or replacement of the ethmoid, frontal, nasal, occipital, parietal, temporal, mandible, maxilla, zygomatic, cervical vertebra, thoracic vertebra, lumbar vertebra, sacrum, rib, sternum, clavicle, scapula, humerus, radius, ulna, carpal bones, metacarpal bones, phalanges, ilium, ischium, pubis, femur, tibia, fibula, patella, calcaneus, tarsal bones or metatarsal bones.

Some aspects of the present invention concern methods of treating a subject that involve implanting a scaffold of the present invention into the subject. In particular embodiments the subject is a vertebrate, such as a mammal, reptile, fish, bird, etc. In particular embodiments the mammal is a human. The subject may be suffering from a bone fracture or a bone defect. The subject may have a bone defect due to trauma, a congenital abnormality, a genetic abnormality a fracture, an iatrogenic defect, a bone cancer, a bone metastasis, an inflammatory disease, an autoimmune disease, a metabolic disease, or a degenerative bone disease.

Other examples of bone diseases or disorders include iatrogenic defects, bone cancer, bone metastases, inflammatory diseases (such as rheumatoid arthritis), autoimmune diseases, metabolic diseases, and degenerative bone disease such as osteoarthritis and osteoporosis. The scaffold may be fabricated for the repair of a simple fracture, compound fracture, or non-union; as an external fixation device or internal fixation device; for joint reconstruction, arthrodesis, arthroplasty, or cup arthroplasty of the hip; for femoral or humeral head or shaft repair or replacement; for femoral head surface replacement or total joint replacement; for repair of the vertebral column, spinal fusion or internal vertebral fixation; for discectomy; for laminectomy; for excision of spinal tumors; for the repairs of a spinal injury; for scoliosis, for lordosis or kyphosis treatment; for for the repair or replacement of the ethmoid, frontal, nasal, occipital, parietal, temporal, mandible, maxilla, zygomatic, cervical vertebra, thoracic vertebra, lumbar vertebra, sacrum, rib, sternum, clavicle, scapula, humerus, radius, ulna, carpal bones, metacarpal bones, phalanges, ilium, ischium, pubis, femur, tibia, fibula, patella, calcaneus, tarsal bones, or metatarsal bones.

D. Kits

In yet another aspect, the present invention provides kits that include a scaffold of the present invention. The scaffold may be sterilely packaged. In some embodiments the kit includes more than one scaffold of the present invention. The kit may include instructions for implanting the scaffold included in the kit. It may further include one or more therapeutic agents that can be administered concurrently or consecutively with implantation of the scaffold. The therapeutic agents include any such agent known to those of ordinary skill in the art, such as any of those agents discussed previously. In some embodiments, the kit includes hardware for placement of the scaffold in the subject, or a device for further shaping the scaffold into a desired configuration. In some embodiments, the kit includes a device for packing in granules into a bony defect.

E. Combination Therapy

Some embodiments of the methods of treatment of the present invention contemplate administering one or more secondary forms of therapy to the subject. For example, a method of treating a bone fracture that involves implantation of one of the scaffolds of the present invention as set forth herein may involve the administration of one or more secondary forms of therapy (e.g., administration of an antimicrobial agent or administration of an anti-inflammatory agent).

The secondary form of therapy can be any type of secondary therapy for the treatment or prevention of a disease or disorder. In particular embodiments, the secondary form of therapy involves administration of one or more additional pharmacologic therapies using conventional methods of administration. Therapy can involve administration of any pharmacological agent, examples of which have been set forth elsewhere in this specification. For example, administration may be oral administration or intravenous administration. Another example of secondary is surgical therapy.

Administration of the compositions of the present invention to a patient will follow general protocols for the administration of therapeutic agent therapy, taking into account the toxicity, if any, of these agents. It is expected that treatment may be repeated as necessary.

F. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Procedure for Porous Calcium Phosphate Scaffold Fabrication 1.1 Polymeric Sponge Template Preparation Selection of the template material: A polyurethane (PU) sponge template is used to produce uniform interconnected porous calcium phosphate scaffolds. This sponge is used to provide the primary structure for the formation of the scaffold struts as well as the formation of secondary microchannels within the scaffold struts. The polyurethane sponge template chosen may range from 45 pores per inch (ppi) to 80 ppi for the inner trabecular core, depending on the final desired pore size. The pore sizes in the inner trabecular core may range from 150 µm to 800 µm after sintering to allow bone cell migration, blood vessel vascularization, and nutrient supply. Additionally, the 80 ppi to 100 ppi polyurethane sponge template or solid calcium phosphate ceramics (with channels and/or pores produced by slip casting) may be chosen for the outer cortical shell, depending on the final desired pore size. The pores and/or channel or holes for the outer cortical shell may be in the range of about 50 µm to about 250 µm after sintering, depending on the desired application place.

Figure 2:
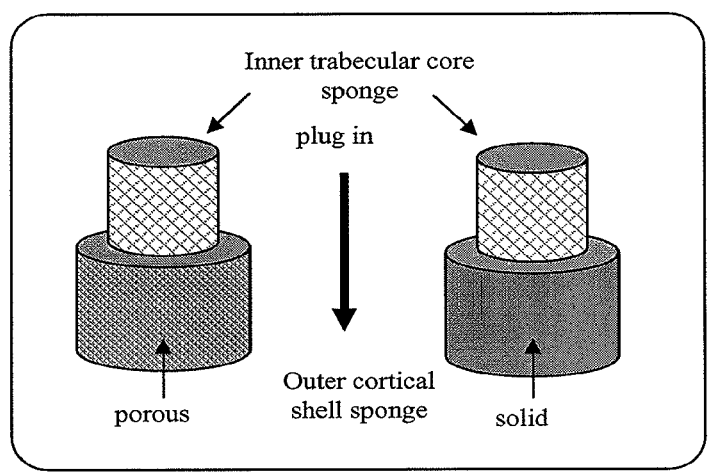
FIG. 2. Schematic showing one example of the making of a bi-layered templates, with the inner trabecular core sponge snuggly fitted into the outer cortical shell sponge.

Template sponge preparation: The polyurethane sponge is used as a template and is first cut to the desired shape and dimension. The cut polyurethane is then ultrasonically treated in 10% to 15% sodium hydroxide (NaOH) solution for 20 to 30 minutes, followed by cleaning in flowing water for 30 to 60 minutes. The treated polyurethane is then rinsed with distilled water. During cleaning with water and rinsing with distilled water, the polyurethane is squeezed and then allowed to expand for 5 to 10 times in order to remove the residual NaOH inside polyurethane sponge template. The polyurethane sponge template is then ultrasonically cleaned again in distilled water for 20 to 30 minutes. This is followed by squeezing the template sponge with paper towel in order to remove excess water. The template sponge is then placed in an oven at 60° C. to 80° C. until completely drying. The completely dried sponge template for the inner trabecular core is then snuggly fitted into the outer sponge template for the cortical shell or solid outer shell (with channels and/or holes depends on final desired structure and application). At this point, as shown in FIG. 2, the sponge template is now one piece (outer cortical shell and inner trabecular core) and is ready for calcium phosphate coating.

1.2 1st Time Coating Calcium Phosphate Slurry Preparation

In order to produce a stable and well-shaped three-dimensional interconnective porous scaffold, a preferred binder is added to the dispersion. The binders used may be carboxymethylcellulose, polyvinyl alcohol, starch, sodium silicate, polyvinyl butyral, methacrylate emulsion, water soluble polyacrylate, polyacrylic acid, polyethylene glygol, etc. In order to avoid slurry agglomeration and cracking of the scaffold during drying, a dispersant and drying agent is added to the dispersion. The preferred binders are polyvinyl alcohol, carboxymethylcellulose and sodium silicate. In this invention, ammonium polyacrylate and N, N-dimethylformamide will be use as a dispersant and a drying agent, respectively. The preferred amount of polyvinyl alcohol, carboxymethylcellulose, sodium silicate, and methacrylate emulsion added are 2% to 4% by mass, 2% to 4% by mass, 1% to 2% by mass and 1%-2% by mass, respectively (based on 100% by mass of calcium phosphate powder).

The polyvinyl alcohol is added to distilled water, heated and stirred until the polyvinyl alcohol is completely dissolved. The solution should be clear after complete dissolution of the polyvinyl alcohol. As the solution is cooled down to room temperature, carboxymethylcellulose is added. After complete dissolution of the carboxymethylcellulose, sodium silicate solution and methacrylate emulsion are added to the mixture and stirred. Additionally 5% to 7% by mass of ammonium polyacrylate dispersant and 3% to 5% by mass of N, N-dimethylformamide drying agent are added to the mixture and stirred continuously. The calcium phosphate powders are then slowly dispersed into the solution, followed by stirring. In this invention, calcium phosphate powder is generic and refers to all the different phases of the calcium phosphate group, including hydroxyapatite, tricalcium phosphate, amorphous calcium phosphate, monocalcium phosphate, dicalcium phosphate, octacalcium phosphate, tetracalcium phosphate, fluorapatite, carbonated apatite and the different mixtures of the different phases. Using continuously slow heating, the solution is slowly stirred in order to evaporate the water content and until a powder/liquid ratio of 1.20 to 1.50 is obtained. The slurry is then allowed to cool down to the room temperature before being used for coating.

1.3 First Time Calcium Phosphate Coating, Drying and Sintering

The treated one piece sponge template containing the outer cortical shell and inner trabecular core (from section 1.1) is then immersed into the calcium phosphate slurry until the calcium phosphate slurry is fully absorbed into the sponge template scaffold. The polyurethane is then rolled on a glass plate with rod bar then allowed to expand for 5 to 10 times in order to remove excess slurry. After removing the excess slurry, some of pores may be clogged up with slurry because of high slurry viscosity. In order to ensure interconnectivity, uniformity, and open pores, the scaffolds are slightly blown with air. In this process, it is preferred that the template is homogeneously coated on the inside and outer the sponge template. If this homogeneous coating is not achieved, the calcium phosphate-coated sponge template scaffold will collapse after sintering or fracture during handling. Additionally, the homogeneous coating is preferred for the successful production of the secondary microchannels within the main scaffold struts.

Based on the thermoanalysis of polyurethane sponge template and nano-size powders, the calcium phosphate-coated sponge template scaffolds dry at 25° C. to 35° C. and at 60%-80% humid environment. Drying time will range from 12 to 72 hours, depending on the size of the sponge template scaffolds. After drying, the calcium phosphate-coated sponge template scaffold typically shrinks about 8% to 10%. After the sponges are completely dried, the coated sponges are then placed on an alumina plate, placed in a high temperature furnace, and sintered for 2 to 5 hours at 1200° C. to 1250° C. using an 8-step sintering profile shown in FIG. 3. Sintering will further shrink the calcium phosphate-coated sponge template scaffolds by 22%-25%.

1.4 Second Time Coating Calcium Phosphate Suspension Preparation

The second time coating is performed to fill up coating defects from first time coating performed in section 1.3. This second time coating will improve the compressive strength of the scaffold and to ensure a more rounded strut to enhance cell attachment. In order to make the second time coating calcium phosphate suspension, different amounts of the same binders and chemical agents used in the first time coating calcium phosphate slurry preparation (section 1.2) are utilized. However, the concentrations of the binders and chemical agents used are different from the $1^{st}$ time coating calcium phosphate slurry preparation (section 1.2). The preferred amount of polyvinyl alcohol, carboxymethylcellulose, sodium silicate, and methacrylate emulsion used in the second time coating calcium phosphate suspension preparation are about 3% to about 7% by mass, about 3% to about 7% by mass, about 1% to about 2% by mass and about 1% to about 2% by mass, respectively (based on 100% by mass of calcium phosphate powder).

The polyvinyl alcohol is added to distilled water, heated and stirred until the polyvinyl alcohol is completely dissolved. The solution should be clear after complete dissolution of the polyvinyl alcohol. As the solution is cooled down to room temperature, carboxymethylcellulose is added. After complete dissolution of the carboxymethylcellulose, sodium silicate solution and methacrylate emulsion are added to the mixture and stirred. Additionally 7% to 10% by mass of ammonium polyacrylate dispersant and 5% to 7% by mass of N, N-dimethylformamide drying agent are added to the mixture and stirred continuously. The calcium phosphate powders are then slowly dispersed into the solution, followed by stirring. Using continuously slow heating, the solution is slowly stirred in order to evaporate the water content and until a powder/liquid ratio of 0.4 to 0.5 is obtained. The slurry is then allowed to cool down to the room temperature before being used for coating.

1.5 Second Coating, Drying and Sintering

Scaffolds after the first coating and sintering (section 1.3) is immersed into second time coating calcium phosphate suspension (section 1.4) for 10 to 20 seconds. After immersion, the scaffolds are removed from the suspension. Most of the scaffold pores will be clogged up by the calcium phosphate suspension. In order to ensure interconnectivity, uniformity, and open pores, the scaffolds are slightly blown with air. The calcium phosphate-coated sponge template scaffolds are then dried at 25° C. to 35° C. and at 60% to 70% humid environment. Drying time will range from 12 to 48 hours, depending on the size of the sponge template scaffolds. After the sponges are completely dried, the coated sponges are then placed on an alumina plate, placed in a high temperature furnace, and sintered for 2 to 3 hours at 1200° C. to 1250° C. using a 5-step sintering profile shown in FIG. 4.

1.6 Solid Outer Shell with Channels and/or Holes Calcium Phosphate Suspension Preparation For scaffolds to be used in loading bearing applications, solid outer shells with channels having diameters ranging from about 100 μm to about 200 μm and/or holes having diameter ranging from about 200 μm to about 500 μm can fabricated by slip casting and freeze drying method. In order to produce a slip casting suspension, the same binders and same chemical agents in section 1.2 as well as section 1.4 are used. The preferred amount of polyvinyl alcohol, carboxymethylcellulose, sodium silicate, and methacrylate emulsion used in the second time coating calcium phosphate suspension preparation are 3% to 7% by mass, 3% to 7% by mass, 0.5% to 1% by mass and 0.5% to 1% by mass, respectively (based on 100% by mass of calcium phosphate powder).

The polyvinyl alcohol is added to distilled water, heated and stirred until the polyvinyl alcohol is completely dissolved. The solution should be clear after complete dissolution of the polyvinyl alcohol. As the solution is cooled down to room temperature, carboxymethylcellulose is added. After complete dissolution of the carboxymethylcellulose, sodium silicate solution and methacrylate emulsion is added to the mixture and stirred. Additionally about 7% to about 10% by mass of ammonium polyacrylate dispersant and about 5% to about 7% by mass of N, N-dimethylformamide drying agent are added to the mixture and stirred continuously. The calcium phosphate powders are then slowly dispersed into the solution, followed by stirring. Continuously slow heat and stir the solution to evaporate the water content until a powder/liquid ratio of about 0.4 to about 0.5 is obtained. The slurry is then allowed to cool down to the room temperature before being used for slip casting.

1.7 Slip Casting, Freeze Dry and Sintering for Solid Outer Shell

The prepared slip casting calcium phosphate suspension is poured into a designed gypsum mold with a polyurethane sponge mesh having about 10 ppi to about 20 ppi. The gypsum mold containing polyurethane sponge is then rolled at 10 to 20 rpm until all water is completely absorbed by the gypsum mold and a desired thickness is achieved. The gypsum mold is then dried using a freeze dryer for a period ranging from 24 to 72 hours. After drying, the solid outer shell is separated from gypsum mold and holes with diameter ranging from 200 μm to 500 μm are drilled through the outer shell. The well-prepared outer shell is then placed in the high temperature furnace and sintered using a 8-step sintering profile shown in FIG. 3. After sintering, the about 10 ppi to about 20 ppi polyurethane sponge mesh is burnt out, resulting in the formation of channels within the shell.

1.8 Antibacterial Calcium Phosphate Sol Preparation

Variable calcium phosphates ceramics such as hydroxyapatite (Ca/P=1.67), tri-calcium phosphate (Ca/P=1.50), meta-calcium phosphate (Ca/P=0.50), calcium polyphosphate (Ca/P=0.50), dicalcium phosphate dehydrate (Ca/P=1.00), monocalcium phosphate anhydrous (Ca/P=0.50) sol can be synthesized using the correct amount of calcium and phosphorous precursors and with controlled aging conditions. Additionally, antibacterial calcium phosphate sol can be synthesized using silver- or zinc-doped in the phosphorous precursor. To make the calcium precursor, a correct amount of calcium nitrate tetrahydrate [$Ca(NO_3)_2 \cdot 4H_2O$ (Aldrich 99%, USA)] is fluxed in sufficient amount of methyl alcohol and is dehydrated at temperatures ranging from 150° C. to 200° C. After solvent evaporation, the calcium precursor is refluxed in sufficient amount of methyl alcohol. In order to make the phosphorous precursor, a correct amount of triethyl phosphite [$(C_2H_5O)_3P$ (Fluka 97%, Japan)] is fluxed in sufficient amount of methyl alcohol. This fluxed phosphorous precursor is also pre-hydrolyzed for 5 hours in the presence of a catalyst (acetic acid [$CH_3COOH$] containing 0.5 mol % to 1.5 mol % of silver nitrate [$Ag(NO_3)$] or 0.5 mol % to 1.5 mol % of zinc nitrate hydrate [$Zn(NO_3)_2 \cdot xH_2O$] and distilled water [$H_2O$]). The silver- or zinc-doped calcium phosphate sol is then synthesized by reacting calcium and phosphorus precursors for a period of 1 to 2 hours and with vigorous stirring. The reaction is performed under an argon atmosphere. The synthesized silver- or zinc-doped calcium phosphate sol is then filtrated through a 0.20 μm to 0.45 μm syringe filter, followed by aging at temperatures ranging from 40° C. to 80° C. and for a period ranging from 12 to 204 hours. After aging, the calcium phosphate sol viscosity will be between about 8.0 cps to about 160 cps, depending on the aging temperature, aging time, methods of sealing the beakers/vials containing the precursor during aging, and whether aging is performed in air circulation or without circulation condition. This means the calcium phosphate sol viscosity will govern the thickness, porosity, and density of the coating layer.

1.9 Calcium Phosphate Sol Coating, Drying and Sintering

The fabricated porous calcium phosphate scaffolds from section 1.5 and 1.7 are immersed in the aged calcium phosphate sol doped with or without silver or zinc. After immersing for 5 to 10 seconds, the scaffolds are removed from the sol and centrifuged to remove excess sol. The calcium phosphate sol coated scaffold is then baked and dried in an oven at temperatures ranging from 50° C. to 100° C. and for a period ranging from 3 to 8 hours. After completely dried, the calcium phosphate sol-coated scaffolds are then heat-treated at temperatures ranging from 600° C. to 700° C. using a muffle furnace in air for a period ranging from 1 hour to 5 hours shown in FIG. 6.

Example 2

Examples of Fabricated Hydroxyapatite Scaffolds

Using the process described in Example 1, an example on how this technology is used to fabricate hydroxyapatite scaffolds coated with silver-doped hydroxyapatite is as follows:

2.1 Polymetric Sponge Template Preparation for bi-layered Porous Scaffold Fabrication:

A 60 ppi (pore per inch) polyurethane sponge template is chosen for trabecular core fabrication and the 100 ppi polyurethane sponge template is chosen for outer cortical shell fabrication. The polyurethane sponge template for the trabecular core is cut to a shape of a solid cylinder with a length of 36 mm and a diameter of 28 mm. The polyurethane sponge template for the outer cortical shell is cut to resemble a cylindrical pipe and is hollow core in the middle. Dimension for the polyurethane sponge template for the outer cortical shell is 36 mm in length, with an outer diameter of 30 mm and an inner diameter of 28 mm, thereby having a 2 mm wall thickness. These polyurethane sponges are ultrasonically treated in 10% sodium hydroxide (NaOH) solution for 20 minutes, followed by cleaning in flowing water for 40 minutes and then rinsed with distilled water. During cleaning, the sponges are squeezed and then allowed to expand for 10 times to remove the residual NaOH inside polyurethane sponge templates. These sponges are then ultrasonically cleaned again in distilled water for 30 minutes. The sponges are then squeezed with paper towels to remove excess water. This is followed by drying at 80° C. in an oven for 5 hours until completely dry is achieved. After completely drying, the polyurethane sponge template for the trabecular core is then snuggly fitted into the pipe-like polyurethane sponge template for the outer cortical shell or pipe-like solid outer shell (with channels and/or holes depends on final desired structure and application). At this point, as shown in FIG. 2, the sponge template is now one piece (outer cortical shell and inner trabecular core).

2.2 First Time Coating Hydroxyapatite Powder and β-tricalcium Phosphate Mixed Slurry Preparation As an example of this invention, nano-sized hydroxyapatite powder and nano-sized β-tricalcium phosphate powder are used for the fabrication of scaffolds because of their ability to sinter. A 3% (by mass) polyvinyl alcohol (molecular weight of 89,000 to 98,000) is added to 20 ml of distilled water, heated on the hot plate to 60° C. and stirred until the polyvinyl alcohol is completely dissolved. The solution should be clear after complete dissolution of the polyvinyl alcohol. As the solution is cooled down to room temperature, a 3% (by mass) carboxymethylcellulose (molecular weight of 10,000; viscosity of 53,000 cps at 25° C.) is added. After complete dissolution of the carboxymethylcellulose, a 1% (by mass) of sodium silicate solution and a 1% (by mass) of methacrylate emulsion are added to the mixture and stirred. Additionally, a 7% (by mass) of ammonium polyacrylate dispersant and a 5% (by mass) of N, N-dimethylformamide drying agent are added to the mixture and stirred continuously. The percentage of these binders and drying agents are based on 100% by mass of calcium phosphate powder. Three grams of hydroxyapatite powder and 3 grams of β-tricalcium phosphate powders are then slowly dispersed into the solution, followed by stirring. Using continuously slow heat, the solution is slowly stirred in order to evaporate the water content and until a powder/liquid ratio of 1.50 is obtained. The slurry is then cool down to the room temperature before being used for coating the polyurethane sponges.

2.3 First Time Calcium Phosphate Coating, Drying and Sintering

The treated one piece sponge template containing the (outer cortical shell and inner trabecular core (from section 2.1) is immersed in the first time coating slurry (from section 2.2) until the calcium phosphate slurry is fully absorbed in the sponge template scaffold. While in the slurry, the immersed polyurethane sponge template is manually compressed with the aid of a stirrer and allowed to expand for 8 times. The sponge template is then removed from the slurry and excess slurry is removed by the sponge on glass plate with a rod bar. After removal of the excess slurry, some of the pores in the sponge template may be clogged with slurry because of the high slurry viscosity. In order to ensure interconnectivity, uniformity, and open pores, the scaffolds are slightly blown with air. Based on the thermoanalysis of polyurethane sponge templates and nano-size powders, the calcium phosphate slurry-coated sponge template scaffolds are then dried at 27° C. (in 80% humidity in still air environment) for 60 hours. After drying, the calcium phosphate-coated sponge template scaffolds shrink by 8%. After completely drying, the sponge template scaffolds are placed on an alumina plate and sintered in a furnace. The dried calcium phosphate coated sponge template scaffolds are sintered by using the 8-step sintering profile shown in FIG. 3. After sintering, the calcium phosphate coated sponge template scaffolds shrink by 22%. In addition to FIG. 3, details of the 8-step sintering profile, with heating rate and final temperature is as follows:

Step 1: heat 2° C./minute until 230° C.
Step 2: heat 1° C./minute until 280° C.
Step 3: heat 0.5° C./minute until 400° C.
Step 4: heat 3° C./minute until 600° C.
Step 5: keep 600° C. for 1 hour.
Step 6: heat 5° C./minute until 1230° C.
Step 7: keep 1230° C. for 3 hours.
Step 8: cool 5° C./minute to room temperature.

2.4 Second Time Coating Calcium Phosphate Suspension Preparation

For the second time coating calcium phosphate suspension, different amounts but the same binders and chemical agents (in section 2.2) are used. A 3% (by mass) polyvinyl alcohol (molecular weight of 89,000 to 98,000) is added to 20 ml of distilled water, heated on a hot plate to 60° C. and stirred until the polyvinyl alcohol is completely dissolved. The solution should be clear after complete dissolution of the polyvinyl alcohol. As the solution is cooled down to room temperature, a 5% (by mass) carboxymethylcellulose (molecular weight of 10,000; viscosity of 53,000 cps at 25° C.) is added. After complete dissolution of the carboxymethylcellulose, a 1% (by mass) of sodium silicate solution and a 1% (by mass) of methacrylate emulsion are added to the mixture and stirred. Additionally, a 10% (by mass) of ammonium polyacrylate dispersant and a 7% (by mass) of N, N-dimethylformamide drying agent are added to the mixture and stirred continuously. The percentage of these binders and drying agents are based on 100% by mass of calcium phosphate powder. 1.5 grams of hydroxyapatite powder and 1.5 grams of β-tricalcium phosphate powders are then slowly dispersed into the solution, followed by stirring. Using continuously slow heat, the solution is slowly stirred in order to evaporate the water content and until a powder/liquid ratio of 0.50 is obtained. The slurry is then cool down to the room temperature before being used for coating.

2.5 Second Coating, Drying and Sintering

The scaffolds from the first time coating and sintering (from section 2.3) are immersed in the second time coating slurry (from section 2.4) for 20 seconds. The scaffold is then removed from the slurry. Most of the scaffold pores may be clogged with slurry because of the high slurry viscosity. In order to ensure interconnectivity, uniformity, and open pores, the scaffolds are slightly blown with air. The calcium phosphate-coated scaffolds are then dried at 30° C. (in 70% humidity in still air environment) for 24 hours. After complete drying, the calcium phosphate-coated are placed on an alumina plate and sintered in a furnace. The dried calcium phosphate-coated scaffolds are sintered by using the 5-step sintering profile shown in FIG. 4. In addition to FIG. 4, details of the 5-step sintering profile, with heating rate and final temperature is as follows:

Step 1: heat 3° C./minute until 600° C.
Step 2: keep 600° C. for 1 hour.
Step 3: heat 5° C./minute until 1230° C.
Step 4: keep 1230° C. for 3 hours.
Step 5: cool 5° C./minute to room temperature.

2.6 Solid Outer Shell with Channels and/or Holes Calcium Phosphate Suspension Preparation In order to make a slip casting suspension, the same binders and same chemical agents (in sections 2.2 and 2.4) are used. A 3% (by mass) polyvinyl alcohol (molecular weight of 89,000 to 98,000) is added to 20 ml of distilled water, heated on the hot plate to 60° C. and stirred until the polyvinyl alcohol is completely dissolved. The solution should be clear after complete dissolution of the polyvinyl alcohol. As the solution is cooled down to room temperature, a 5% (by mass) carboxymethylcellulose (molecular weight of 10,000; viscosity of 53,000 cps at 25° C.) is added. After complete dissolution of the carboxymethylcellulose, a 0.5% (by mass) of sodium silicate solution and a 0.5% (by mass) of methacrylate emulsion are added to the mixture and stirred. Additionally, a 10% (by mass) of ammonium polyacrylate dispersant and a 7% (by mass) of N, N-dimethylformamide drying agent are added to the mixture and stirred continuously. The percentage of these binders and drying agents are based on 100% by mass of calcium phosphate powder. 1.5 grams of hydroxyapatite powder and 1.5 grams of β-tricalcium phosphate powders are then slowly dispersed into the solution, followed by stirring. Using continuously slow heat, the solution is slowly stirred in order to evaporate the water content and until a powder/liquid ratio of 0.50 is obtained. The slurry is then cool down to the room temperature before being used for slip casting.

2.7 Slip Casting, Freeze Dry and Sintering for Solid Outer Shell

The prepared slip casting calcium phosphate suspension is poured into a 33 mm length by 27 mm diameter gypsum mold containing a 10 ppi polyurethane sponge mesh. The mold is rolled at 12 rpm until all water is completely absorbed by the gypsum mold and a desired 2 mm thickness is achieved. The gypsum mold is then dried using a freeze dryer for 48 hours. After drying, the solid outer shell is separated from gypsum mold and drilled holes having diameter of 300 μm. In order to fabricate a bi-layered scaffold, the $1^{st}$ calcium phosphate-coated trabecular core sponge template (section 2.3) is then snuggly fitted into the dried solid outer shell and dried at 27° C. (in 80% humidity and still air environment) for 60 hours. After complete drying, the bi-layered scaffolds are placed on an alumina plate and sintered in a furnace. The dried calcium phosphate-coated scaffolds are sintered by using the 8-step sintering profile shown in FIG. 3 (section 2.3). Following sintering, the bi-layered coatings are then coated using the $2^{nd}$ time coating calcium phosphate suspension preparation (section 2.4) and sintered using the $2^{nd}$ coating, drying and sintering procedure (section 2.5).

2.8 Antibacterial Calcium Phosphate Sol Preparation

Figure 5:
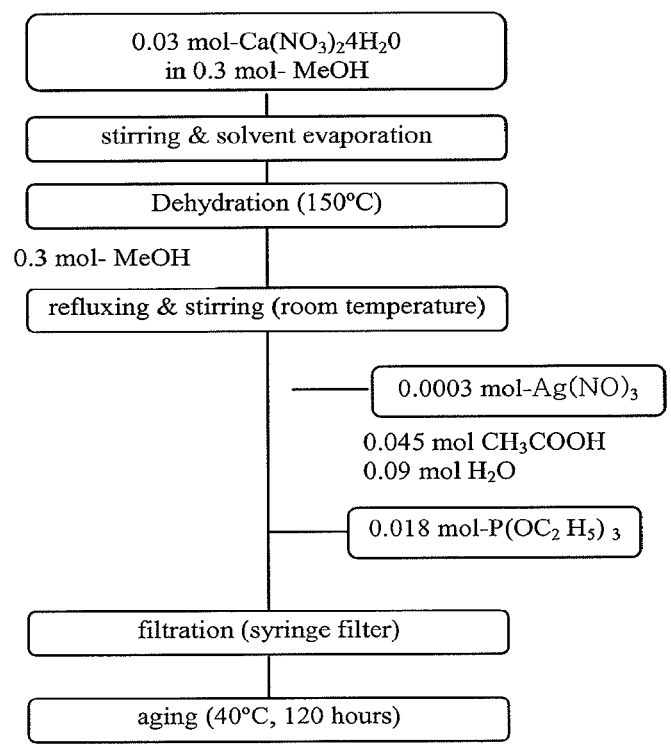
FIG. 5. Flow chart showing a process for producing silver-doped hydroxyapatite sol.

In this invention, silver-doped hydroxyapatite solution is prepared by fluxing 0.03 mol calcium nitrate tetrahydrate [$Ca(NO_3)_2 \cdot 4H_2O$ (Aldrich 99%, USA)] in 0.3 mol methyl alcohol and is dehydrated at 150° C. After solvent evaporation, the calcium precursor is refluxed in 0.3 mol methyl alcohol for 1 hour. The 0.018 mol triethyl phosphite [$(C_2H_5O)_3P$ (Fluka 97%, Japan)] is fluxed in 0.15 mol methyl alcohol and pre-hydrolyzed for 5 hours in the presence of a catalyst (0.045 mol acetic acid [$CH_3COOH$] with 0.0003 mol silver nitrate [$AgNO_3$)] and 0.09 mol distilled water [$H_2O$]). The silver-doped hydroxyapatite sol is then synthesized by reacting calcium and phosphorus precursors for 1 hour with vigorous stirring. All work is performed under an argon atmosphere. The synthesized silver-doped hydroxyapatite sol is then filtrated through a 0.45 μm syringe filter and aged at 40° C. for 120 hours. After aging, the viscosity of the silver-doped hydroxyapatite sol viscosity is 36 cps. The flow chart of the silver-doped hydroxyapatite sol preparation is shown in FIG. 5.

2.9 Calcium Phosphate Sol Coating, Drying and Sintering

The fabricated porous calcium phosphate scaffold is immersed in the aged silver-doped hydroxyapatite sol for 5 seconds. The scaffold is then removed from the sol and centrifuged for 10 seconds at 1000 rpm to remove excess sol. The silver-doped hydroxyapatite sol-coated scaffold is immediately baked and dried for 5 hours at 70° C., followed by a heat treatment at 650° C. for 3 hours using the following 3-step heating profile (FIG. 6):

Step 1: heat 3° C./minute until 650° C.
Step 2: keep 650° C. for 3 hours.
Step 3: cool 3° C./minute to room temperature.

Example 3

Examples of Properties of Hydroxyapatite Scaffolds

The materials discussed below were prepared by the methods of Example 1 and Example 2.

3.1 Polymeric Sponge Template

Figure 7:
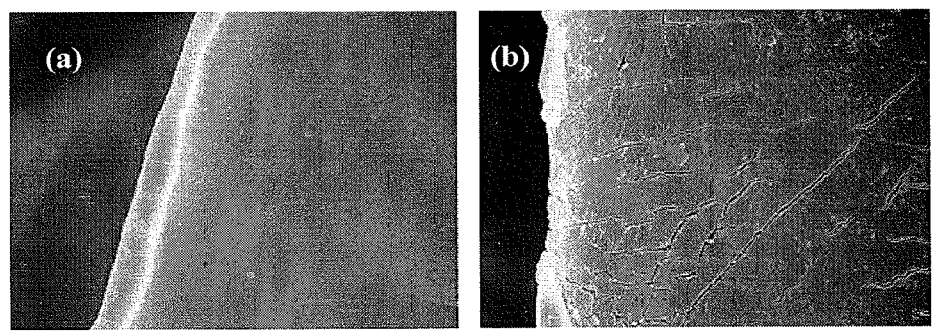
FIG. 7. Representative scanning electron micrographs showing a) the untreated surface of the sponge template, and b) the polyurethane sponge surface after a 20 minute treatment in 10% NaOH. Microcracks on the treated sponge surface are observed and these cracks allow the nucleation of calcium phosphate coatings and ensure the uniformity of the coating on the sponge surface.

After 20 minutes of treating the polymeric sponge template with 10% sodium hydroxide, the surface of the sponge is changed from smooth to rough and is more hydrophilic. As shown in FIG. 7, the shape of the originally cut sponge remains intact, together with its elastic property.

3.2 First Time Calcium Phosphate Coated, Dried and Sintered Scaffold

After immersing the treated polyurethane sponge template in a first time coating slurry followed by drying at 27° C. in a 80% humidity environment for 60 hours, the bi-layered calcium phosphate coated sponge template appears hardened. The coated surface also appears dense and smooth, with only a few cracks observed. Additionally, the scaffold shrinks by 8%.

Figure 3:
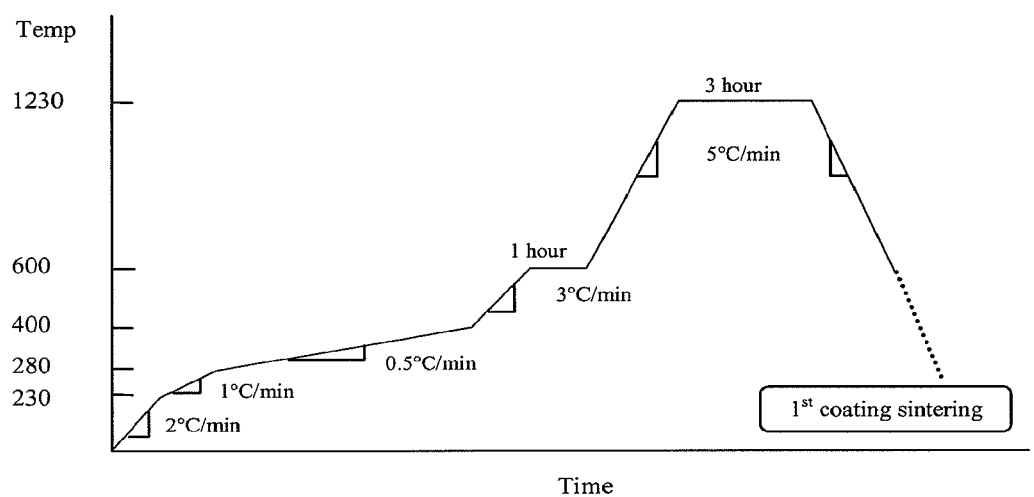
FIG. 3. An exemplary 8-step sintering profile of a calcium phosphate-coated polyurethane sponge after the first calcium phosphate coating procedure.
Figure 8:
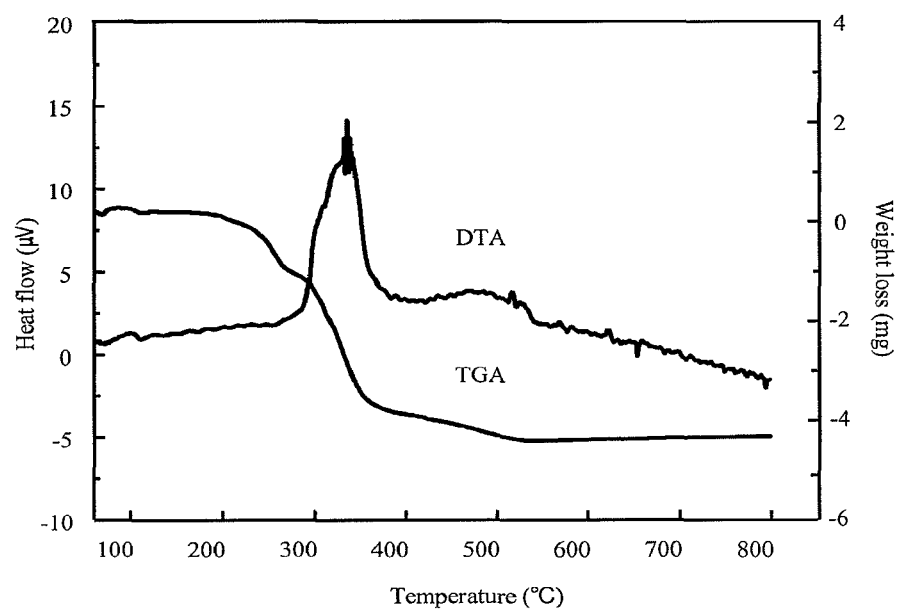
FIG. 8. TG/DTA curve of a polyurethane sponge template.

After sintering the coated sponge using a 8-step sintering profile shown in FIG. 3, the resulting scaffolds appear strong, with uniform coating and well interconnected. The sintered scaffold shows 87% porosity as measured using a gas chromatography method. The compressive strength of sintered scaffold is in the range of the compressive strength of the human cancellous bone (2-180 MPa). As shown in FIG. 8, the TG/DTA curve of polyurethane sponge indicates that the polyurethane sponge burn out occurs from 230° C. Violent burn out of the sponge occurs at temperature from 280° C. to 400° C., with the triangular scaffold struts remaining interconnected after the sponge burn out. Length of the triangular secondary microchannels inside the strut is 40 μm on each side. During this temperature range, the powders in the slurry become semi-molten, thereby allowing viscous flow of the powders and resulting in neck formation between powders.

Figure 9:
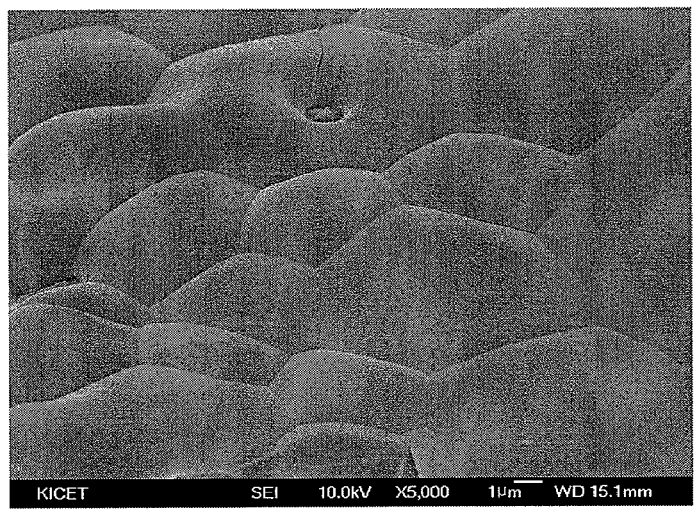
FIG. 9. Representative scanning electron micrograph showing a dense and smooth scaffold surface after sintering (magnification×5,000). Grain boundaries of calcium phosphate on the scaffold surface are also observed.
Figure 10:
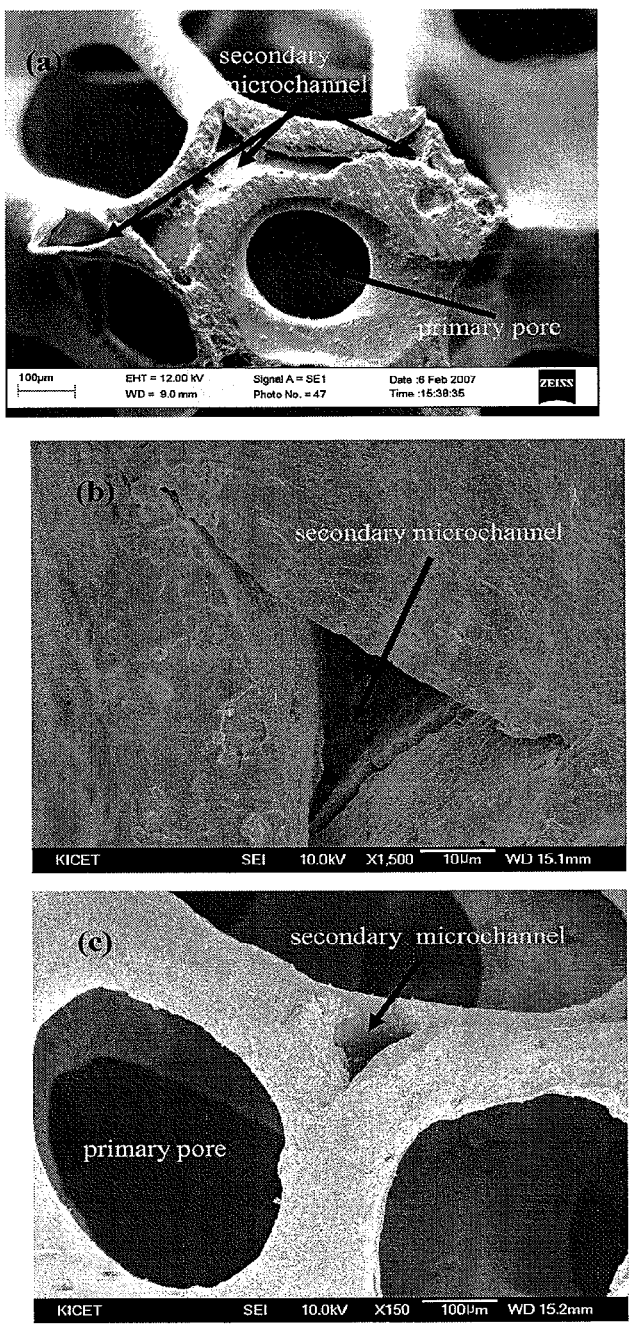
FIGS. 10A-C. Representative scanning electron micrographs (SEM) of a scaffold of the present invention after $2^{nd}$ sintering showing a) cross-section of the interconnecting secondary microchannels within the strut, b) high magnification (magnification×1,500) of the strut showing the triangular secondary microchannel, with length of each side ranging from 30 μm to 120 μm, and c) a primary pore having diameter ranging from 150 μm to 750 μm (magnification×150).

At temperatures between 400° C. to 600° C. and between 600° C. to 1230° C., the calcium phosphate-coated layer interconnects the pores and coarsened the coated surfaces, respectively. Densification of the coated layer occurs when scaffold is sintered at 1230° C. for 3 hours. After sintering, the calcium phosphate scaffolds appears to shrink by 22%. The sintered scaffold surface is dense and smooth, with shown clear grain boundaries as observed using a scanning electron microscopy (FIG. 9). Cross-sectioning of the scaffold shows the presence of triangle shape secondary microchannels within the triangular struts (FIG. 10). The function of these secondary microchannels is to allow the transport and diffusion of nutrients and waster when the scaffold is implanted in the human bone. These features allow the regenerated bone tissues to be kept alive and functional over time.

3.3 Second Time Calcium Phosphate Coated, Dried and Sintered Scaffold

Figure 4:
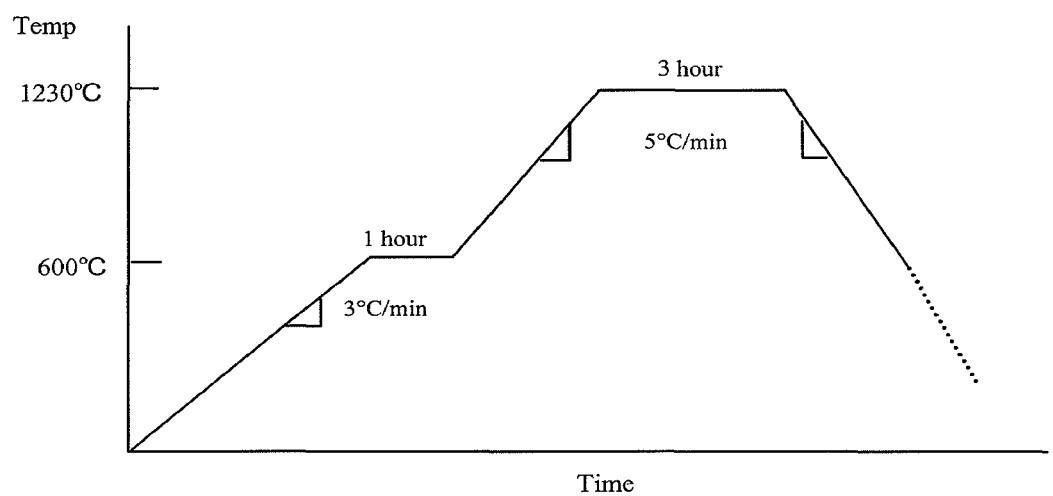
FIG. 4. An exemplary 5-step sintering profile for second coated calcium phosphate scaffold sintering procedure.
Figure 11:
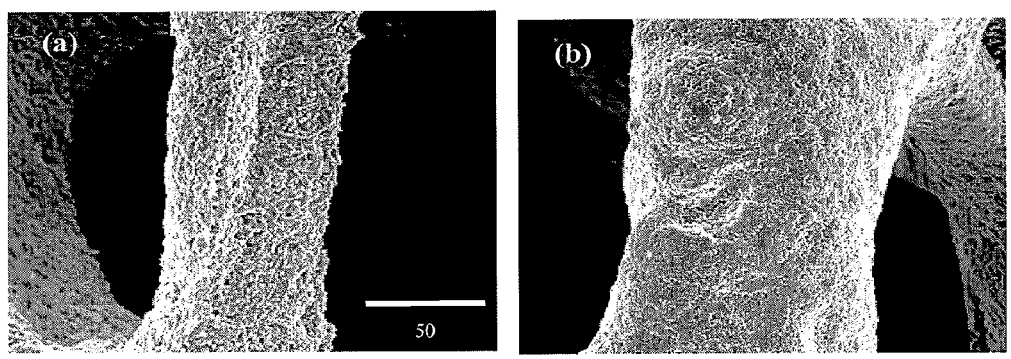
FIGS. 11A-B. Representative scanning electron micrographs (SEM) showing the surface and thickness of a strut after a) $1^{st}$ time coating and sintering, and b) $2^{nd}$ time coating and sintering.

After immersing the first time coating and sintering in the second time coating slurry, followed by drying at 30° C. in a 70% humidity environment for 24 hours, the coated surface appears dense and smooth, but is slightly thicker than first time coated surface (FIG. 11). Sintering of the scaffold using a 5-step sintering profile (as shown in FIG. 4) occurs after drying, with the scaffold shape and size remaining intact after shrinking. No additional shrinkage occurs during the second time coating process. Additionally, there is no change in the size of the secondary microchannels. The final grain size of sintered scaffold surface remains the same as the observations made on the first time coating and sintered scaffold.

Figure 12:
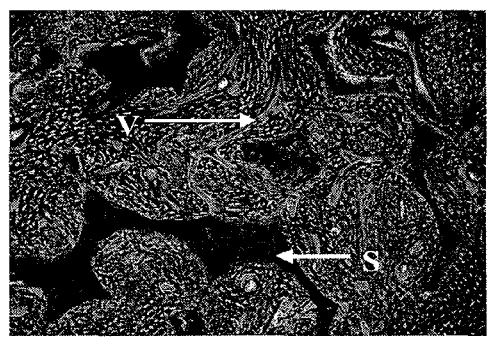
FIG. 12. Representative cross section of a calcium phosphate scaffold infiltrated with bone tissue and vascular ingrowth after 12 weeks post surgery, 200× (S=scaffold, V=vessel). This histological section is viewed under a phase contrast microscope.
Figure 13:
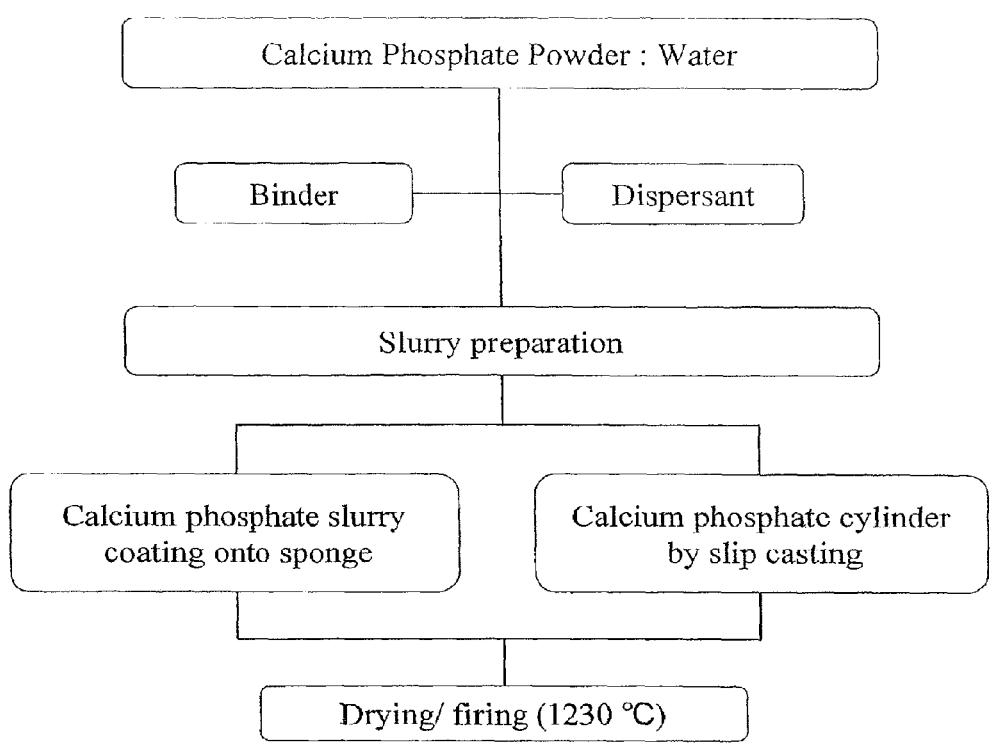
FIG. 13. A non-limiting method of the present invention.
Figure 14:
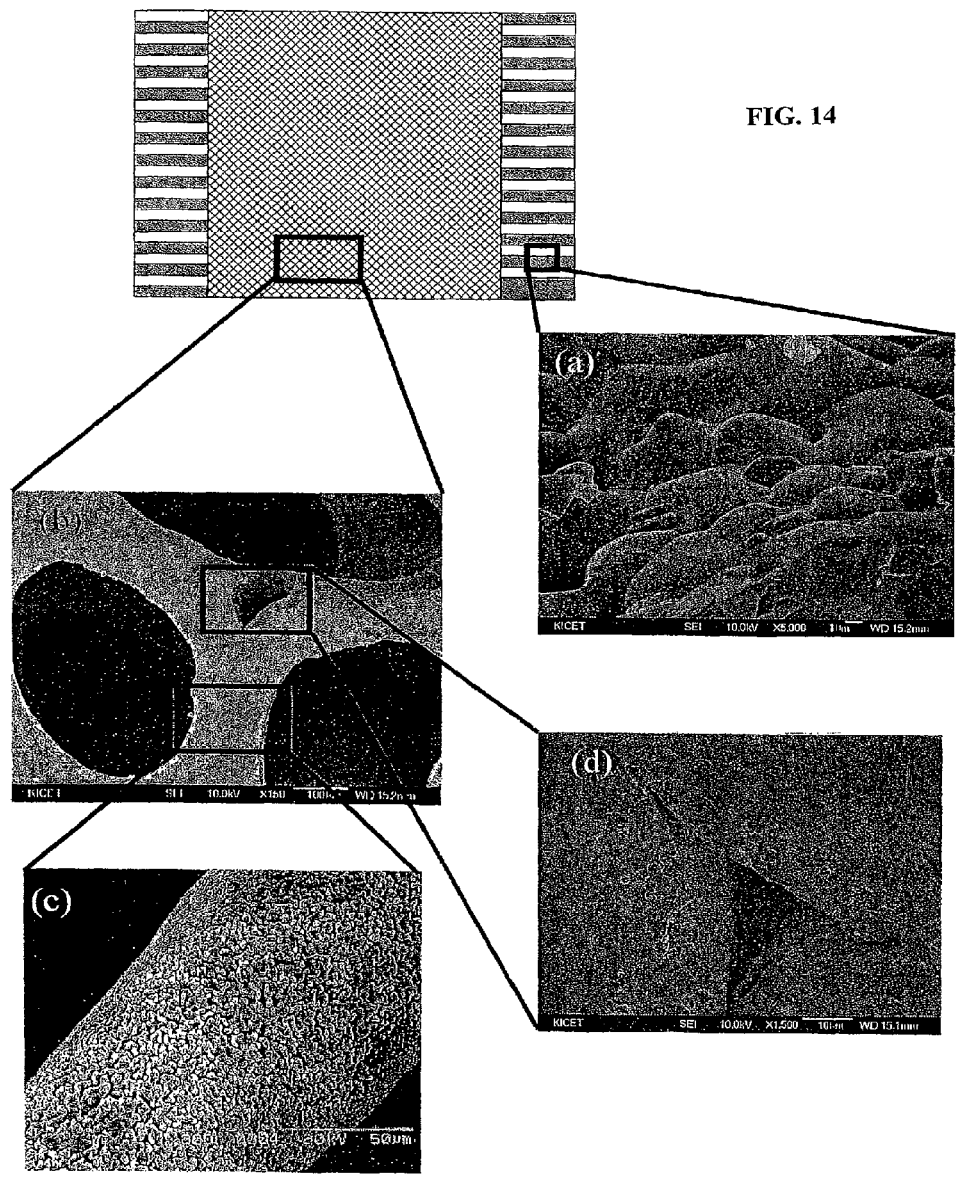
FIGS. 14A-D. Scanning electron microscopy of different cross sections of one scaffold of the present invention showing (FIG. 14A)—outer cortical shell with microchannel.
Figure 15A:
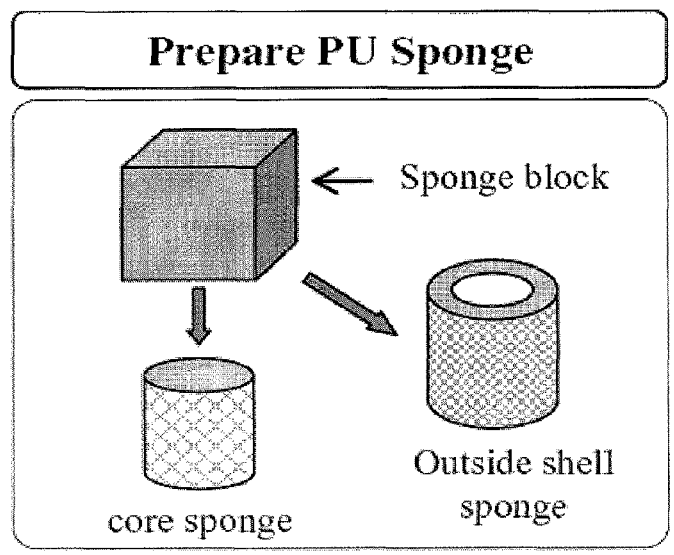
FIGS. 15A-XX. A pictorial description of a method of preparing a scaffold of the present invention. Comments regarding certain figures are as follows.
Figure 15D:
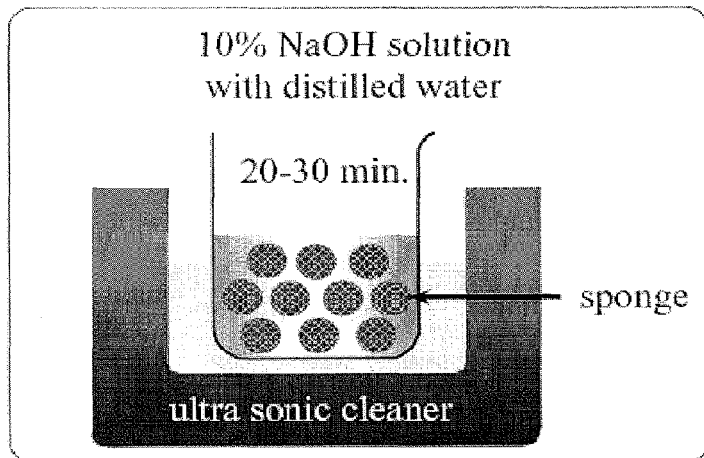
FIG. 15C-G. To change PU sponge surface characteristics from hydrophobic to hydrophilic and increase wetability, a prepared PU sponge may be ultrasonically treated in 10% NaOH solution for 20-30 minutes prior to use. Cleaning with flowing water for 15-20 minutes followed. During cleaning, the sponge may be squeezed and expanded 3-4 times to rinse residual NaOH inside the PU sponge. Ultrasonically cleaning with distilled water for 15-20 minutes may follow. After removing water with, e.g., a paper towel, the sponge may be placed in a 60-80° C. oven until completely dry (e.g., 80° C. for 5 hours).
Figure 15E:
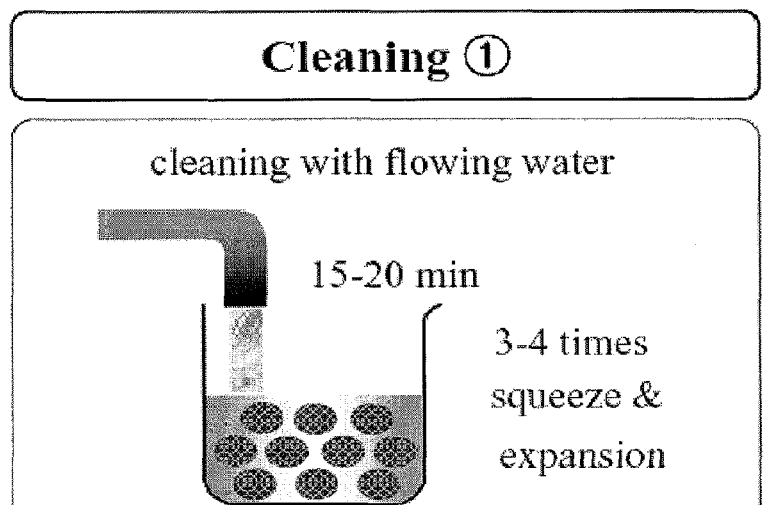
Figure 15F:
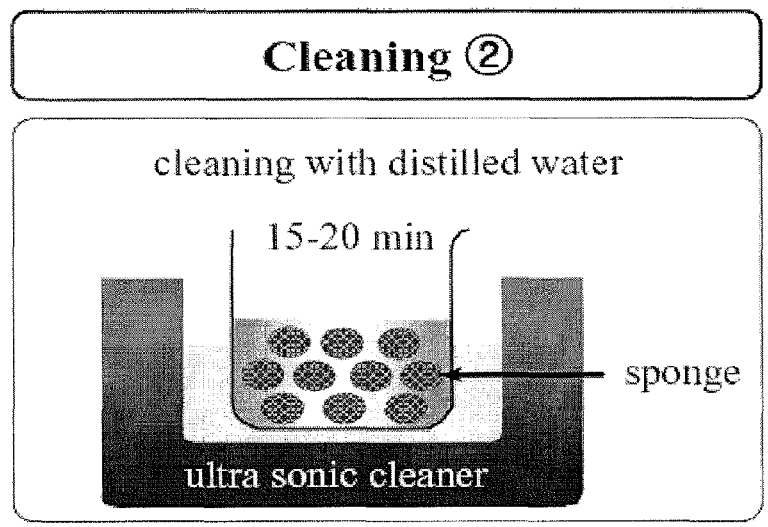
Figure 15G:
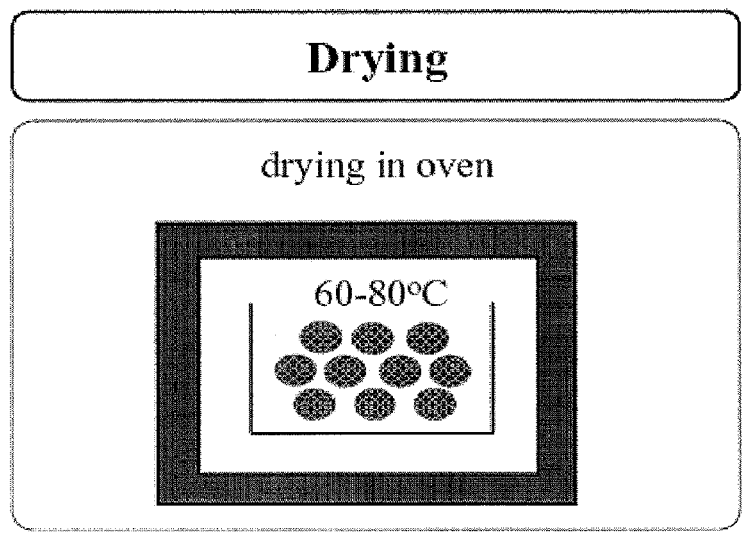
Figure 15H:
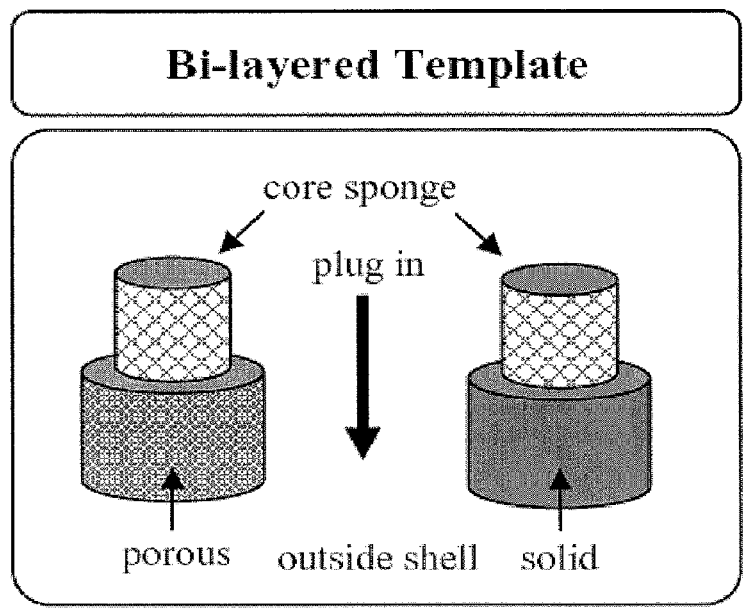
FIG. 15H. After completely drying the core sponge (cancellous bone part), it may be plugged into an outside shell (cortical bone part) porous sponge or solid shell depending on what is desired in the final structure and application.
Figure 15L:
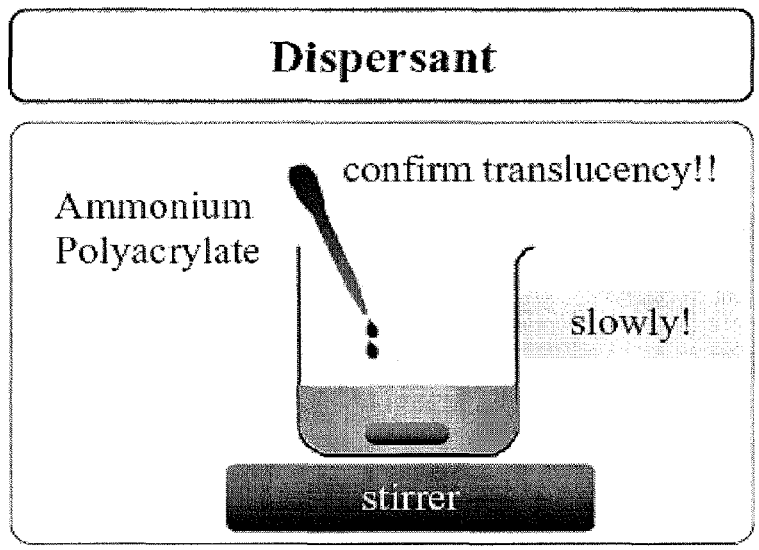
FIG. 15L. To keep homogeneity and prevent rapid sedimentation of calcium phosphate powder, ammonium polyacrylate may be added (e.g., 5-10% by mass based on 100% by mass of powder for dispersant).
Figure 15M:
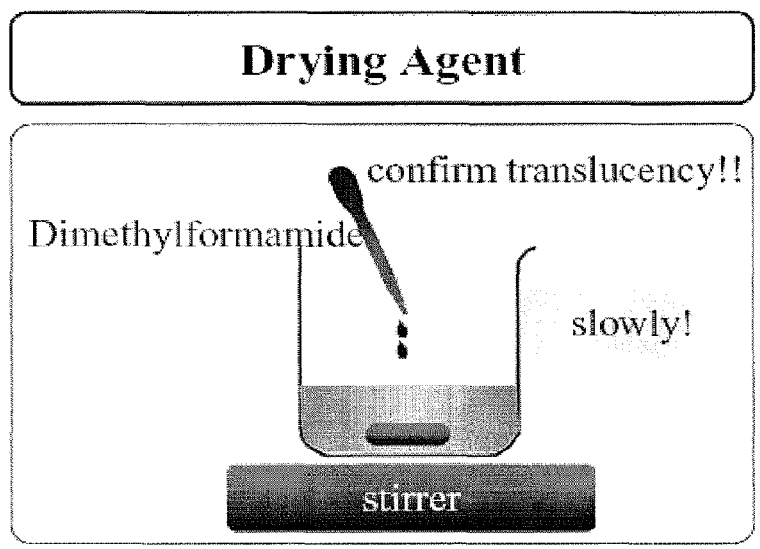
FIG. 15M. To prevent cracks due to rapid drying during the drying process, N,N-dimethylformamide may be added (e.g., 10-15% by mass based on 100% by mass of powder for drying agent).
Figure 15N:
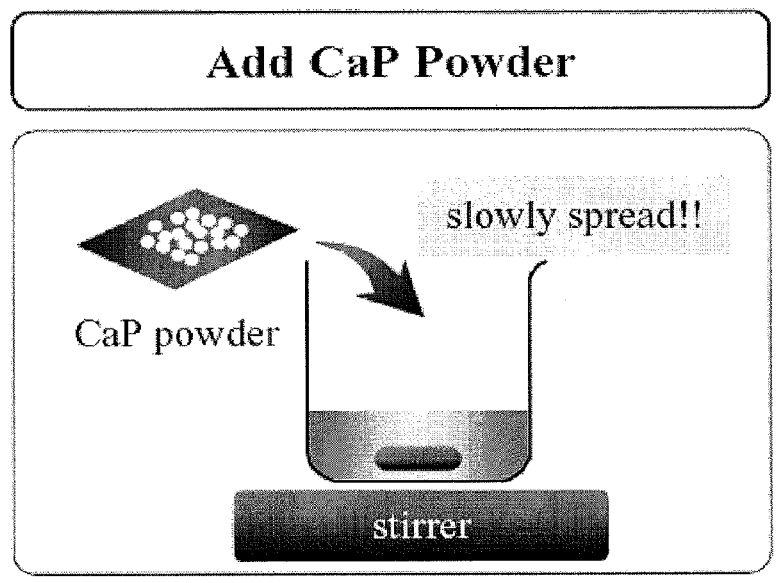
FIG. 15N. To make the calcium phosphate slurry, calcium phosphate powder is slowly spread into the solution.
Figure 15O:
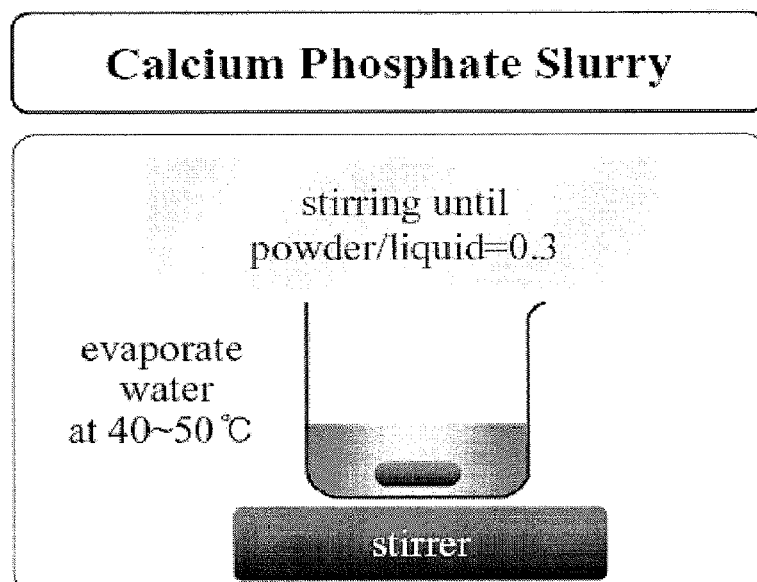
FIG. 15O. After adding the calcium phosphate powder, further stirring is conducted and also the slurry is heated at 40-50° C. for water evaporation during stirring until the powder/liquid ratio is 0.3-0.4.
Figure 15P:
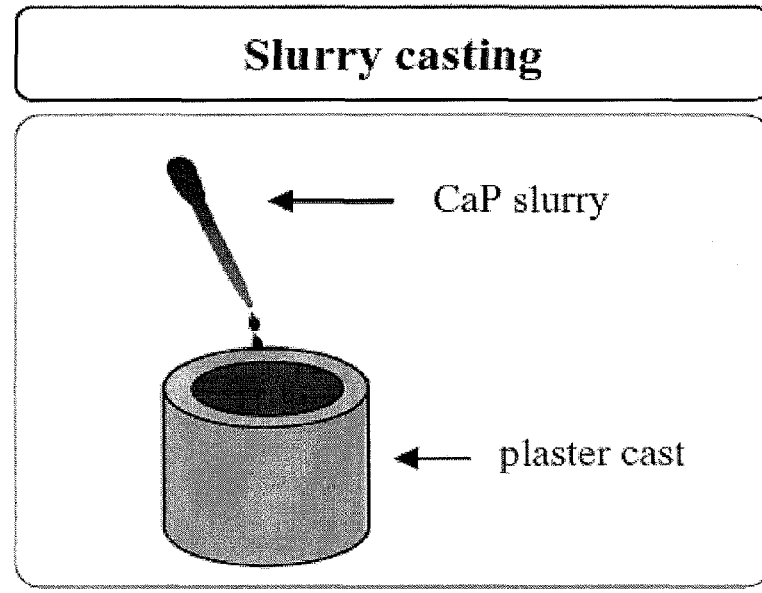
FIG. 15P. Calcium phosphate slurry may be poured plaster cast mold for casting solid outside shell. After the slurry is poured, the plaster cast mold is rotated to obtain a homogeneously thick solid outside shell. This may be repeated several times until the desired outside shell thickness is achieved.
Figure 15Q:
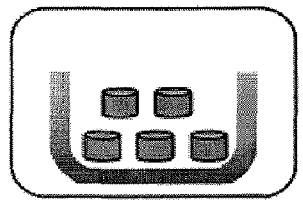
FIG. 15Q. After the solid outside green body shell is completely casted, it may be dried at 30° C. and above 80% humidity in a chamber. The green body may then be separated from the plaster cast mold and dried at 25° C., under 30% humidity air conditions, for 6-24 hours depending on green body size. It is then placed into a furnace for sintering.
Figure 15Q:
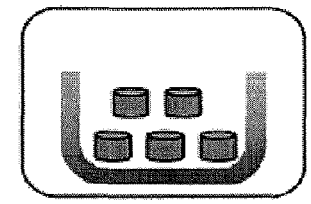
Figure 15R:
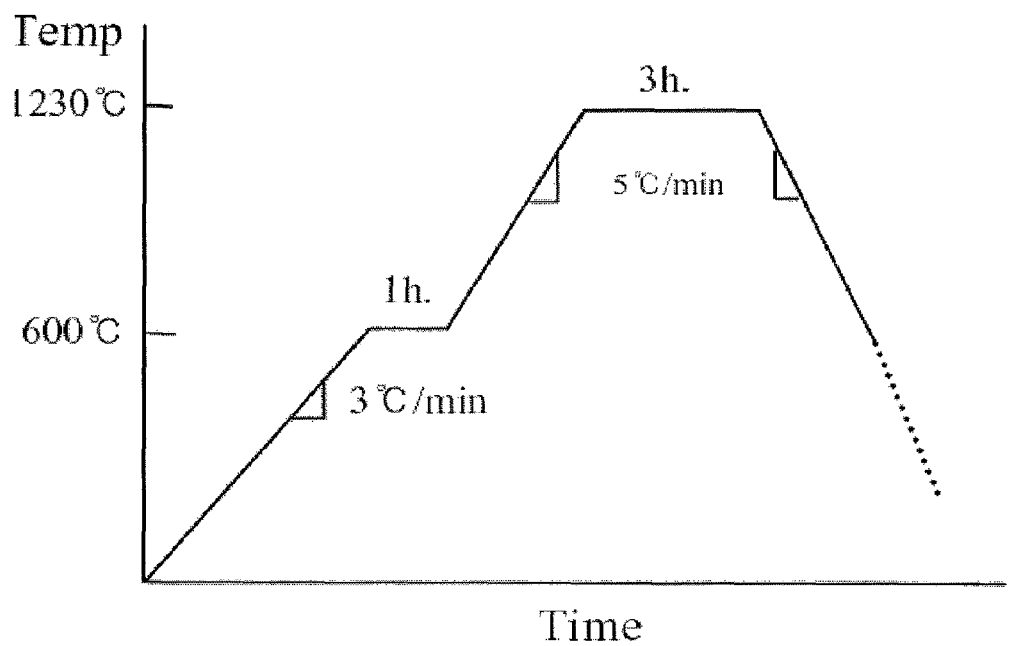
FIG. 15R. First step: heat until 600° C.
Figures 15S, 15T, 15U:
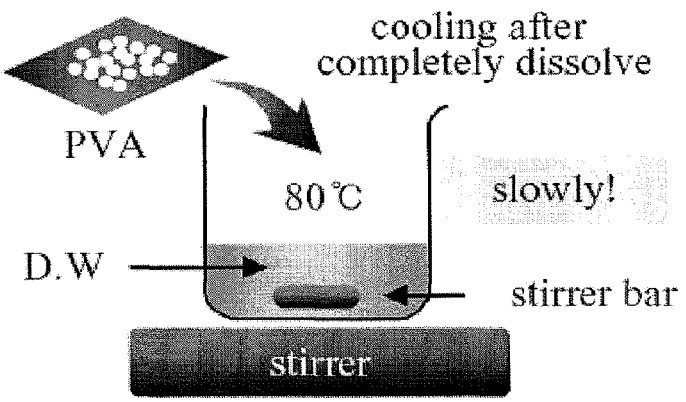
FIG. 15T-U. To make the 1st coating calcium phosphate paste, a binder is preferably added to the dispersion. Such binders are described herein. After adding polyvinyl alcohol into distilled water, further stirring is conducted until all is completely dissolved; then sodium silicate solution is added with continued stirring.
FIG. 15SS. The silver- or zinc- doped calcium phosphate sol is prepared by synthesizing the calcium (Ca), silver (Ag) precursor and the phosphorus (P) precursor.
Figure 15V:
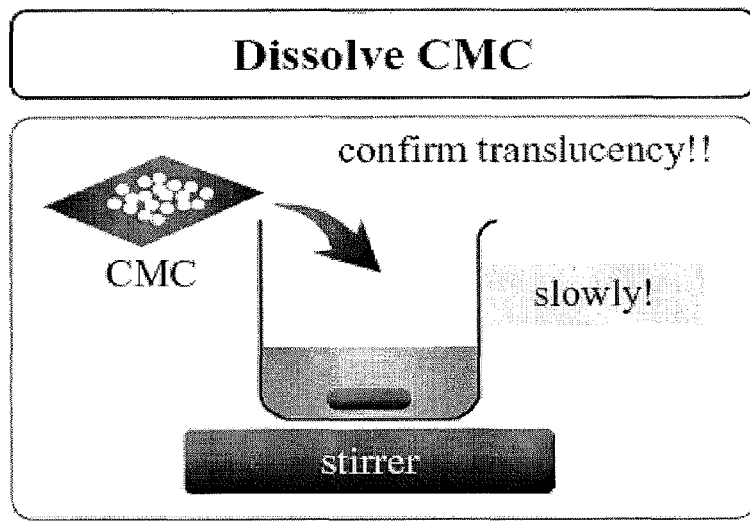
FIG. 15V-W. The amount of carboxymethylcellulose as shown in this figure added is preferably 3-5% by mass. After adding carboxymethylcellulose into solution, further stirring is conducted until all is completely dissolved, then ammonium polyacrylate is added (3-5% by mass based on 100% by mass of calcium phosphate powder) with stirring.
Figure 15W:
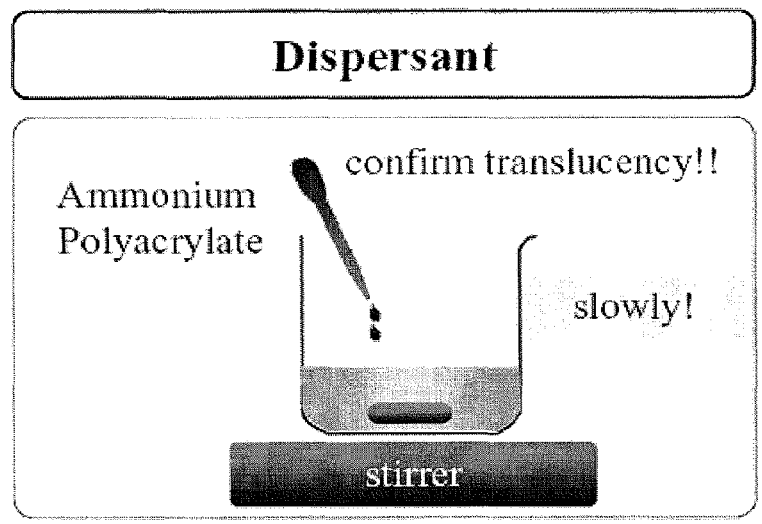
Figure 15X:
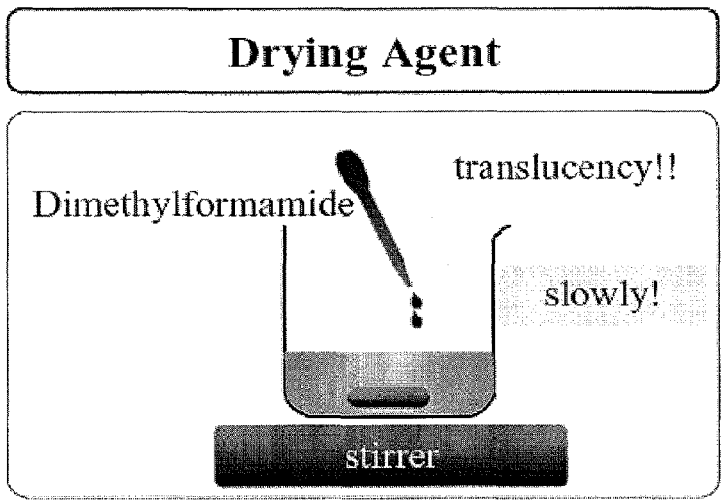
FIG. 15X. To prevent cracks due to rapid drying during the drying process, N,N-dimethylformamide may be added (e.g., 5-10% by mass amount based on 100% by mass of powder for drying agent).
Figure 15Y:
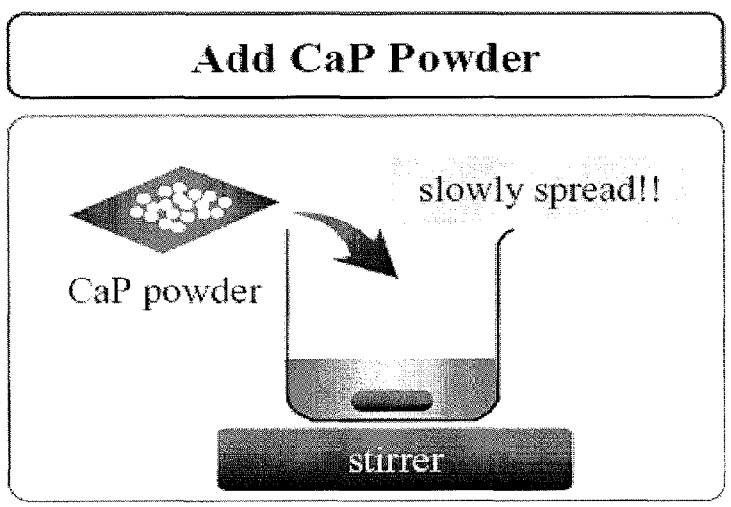
FIG. 15Y. The calcium phosphate slurry may be made by slowly spreading calcium phosphate powder into the solution.
Figure 15C:
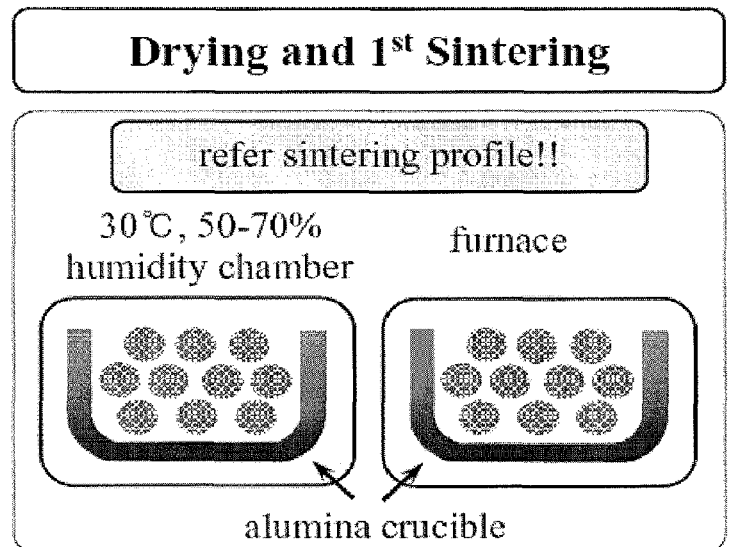
Figure 15D:
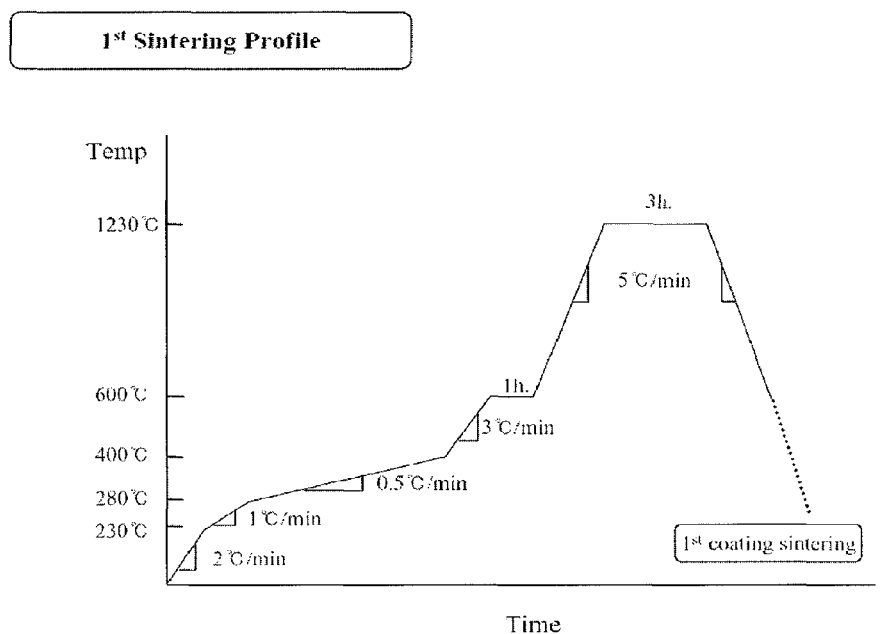
Figure 15H:
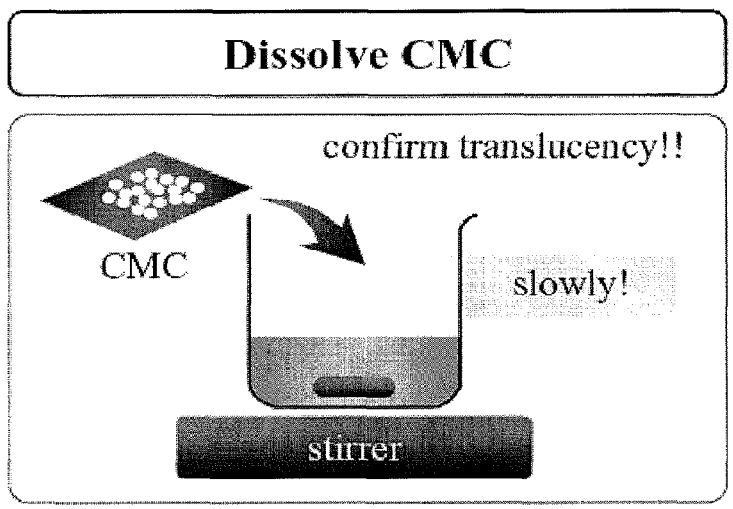
Figure 15I:
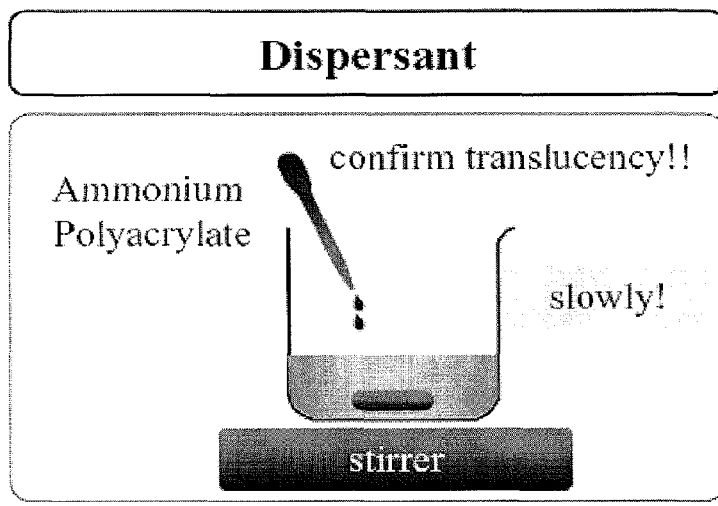
FIG. 15J-K. To make a slip casting slurry, a binder is preferably added to the dispersion. The binders may be carboxymethylcellulose (CMC), polyvinyl alcohol, starch, sodium silicate, polyvinyl butyral, methacrylate emulsion, water soluble polyacrylate, polyacrylic acid, polyethylene glygol, etc. A particularly preferable binder, in certain embodiments, is carboxymethylcellulose and sodium silicate. The amount of carboxymethylcellulose added is preferably 5-10% by mass and sodium silicate solution added is preferably 2-5% by mass based on 100% by mass of calcium phosphate powder. After adding carboxymethylcellulose into distilled water, further stirring is conducted until completely dissolved then add sodium silicate solution and stirring.
FIG. 15BB. The pre-treated bi-layered PU sponge is immersed in the calcium phosphate paste then squeezed and expanded 5-7 times using a Teflon bar. Excess paste is removed with air to avoid the primary pores being filled with paste. The homogeneous coating may be examined using a stereo microscope.
Figure 15N:
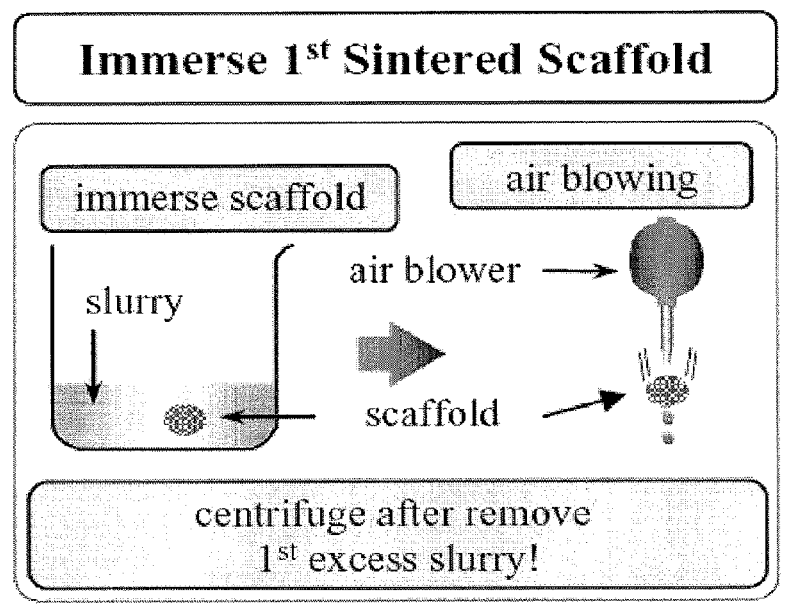
Figure 15O:
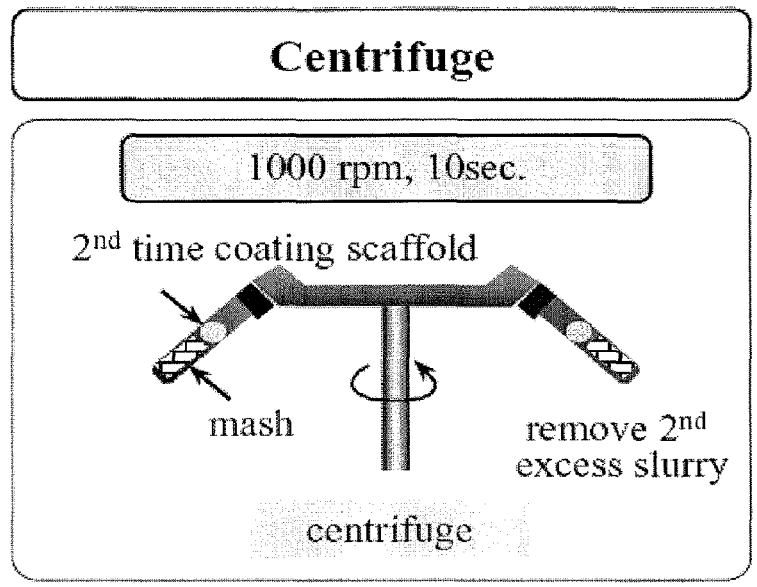
Figure 15P:
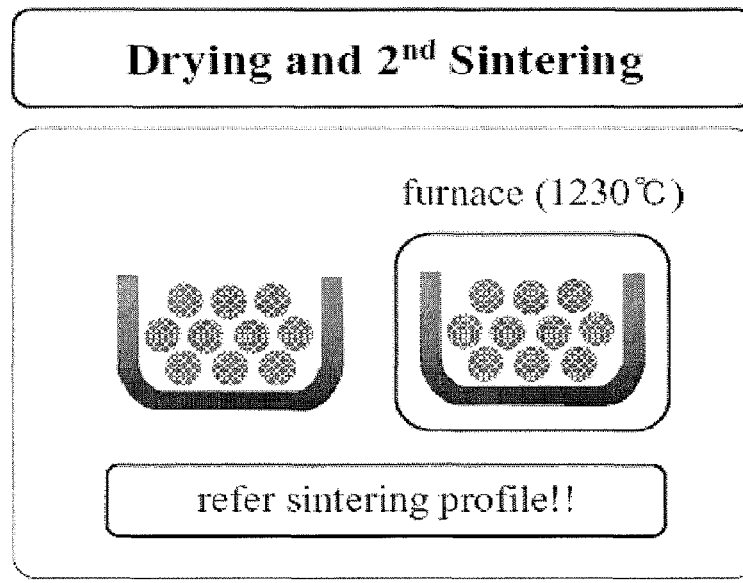
Figure 15Q:
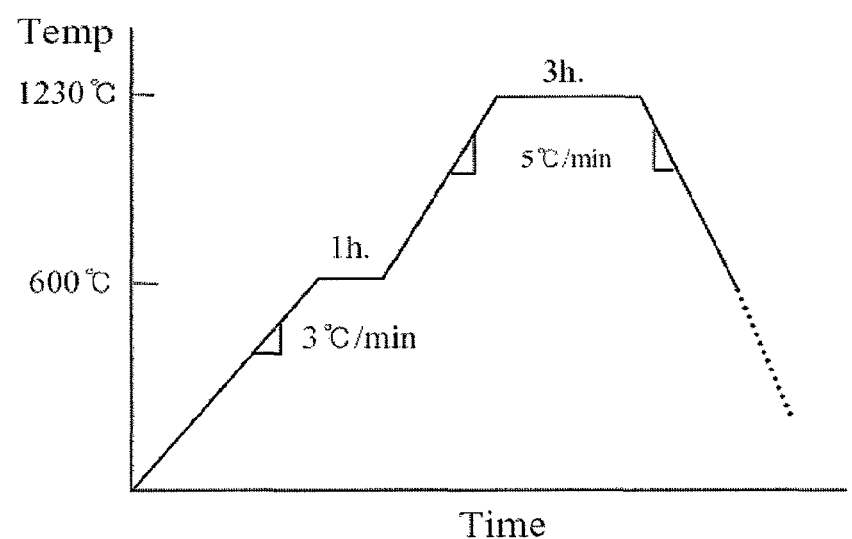
Figure 15U:
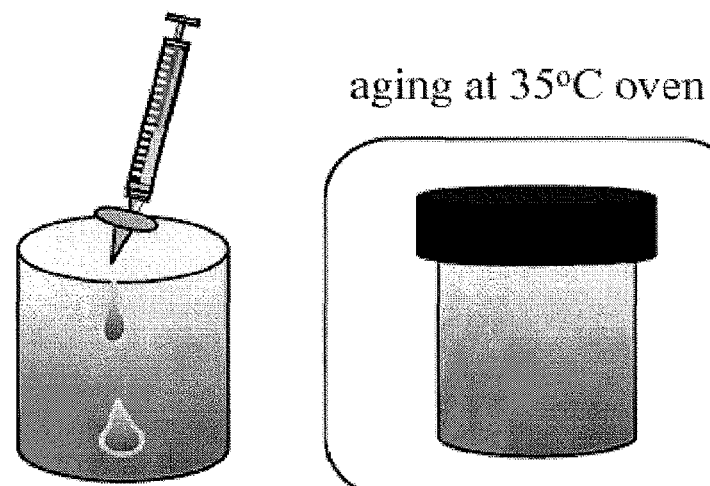
Figure 15V:
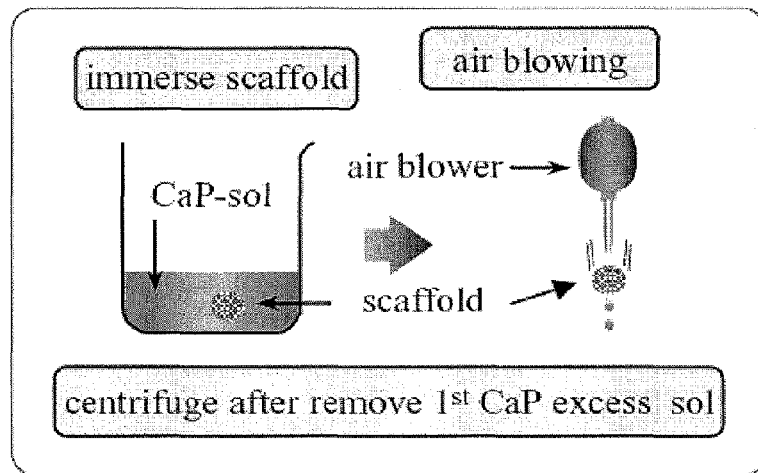
Figure 15W:
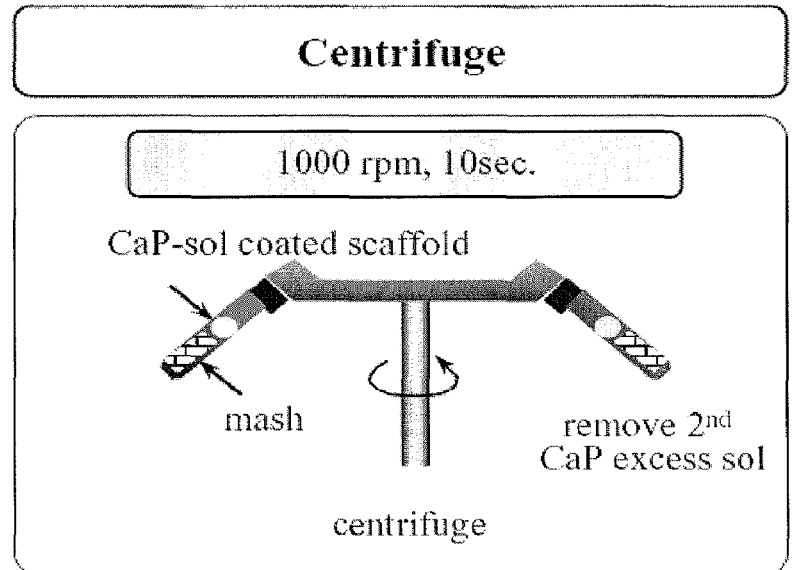
Figure 15X:
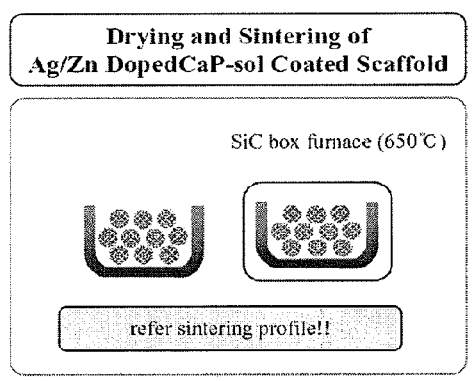
Figure 15X:
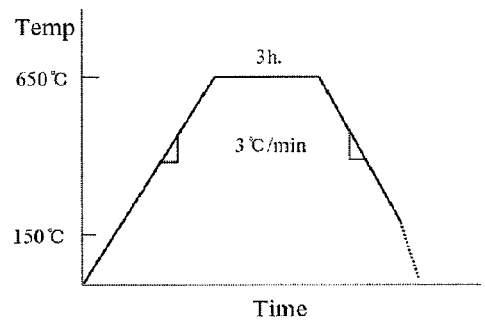

The triangular-shaped strut observed during the first time coating and sintering process becomes rounded after the second time coating and sintering process (FIG. 11). This rounded strut shape is friendlier for encouraging bone or osteoblast cells to attach on the scaffold surface when compared to the triangular-shaped strut. Additionally, in this invention, the complete interconnectivity and uniformity in the pores allow bone/osteoblast cell migration to the center of scaffold. The ability to allow cells to migrate throughout the entire scaffold also means that communications between bone/osteoblast cells in the scaffolds are not hindered. In addition to the complete interconnectivity and uniformity in the pores, continuous secondary microchannels within the struts also allow the transport of blood, nutrients, and wastes between the implanted scaffold and natural bone as well as within the scaffolds. These functional structures (interconnectivity and uniform pores as well as secondary microchannels) also allow the bridging of the scaffolds to the natural bone by the bone/osteoblast cells and vascular ingrowth (FIG. 12).

Figure 6:
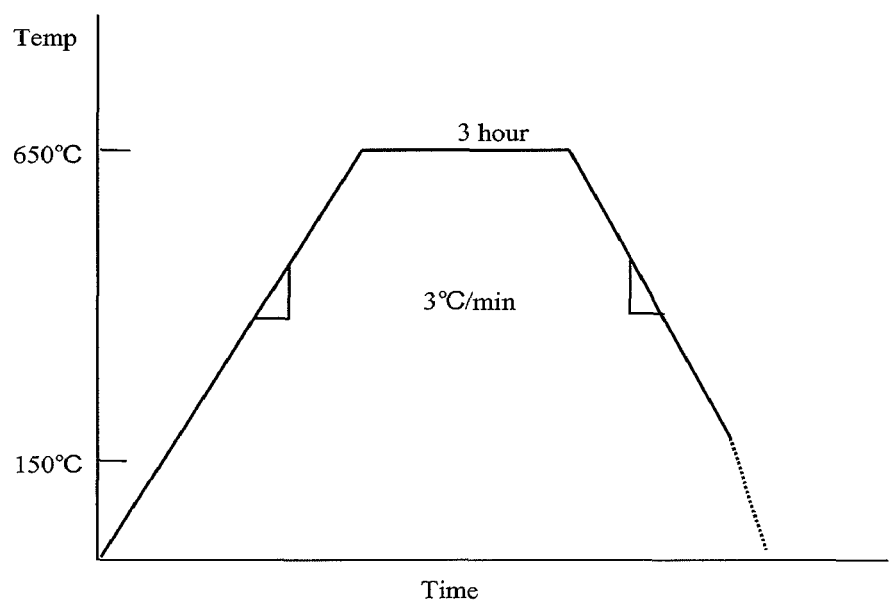
FIG. 6. An exemplary 3-step sintering profile of a scaffold after coating the scaffold with or without silver- or zinc-doped calcium phosphate sol.

3.4 Antibacterial Silver-Doped Hydroxyapatite Sol Coating, Drying and Sintering Antibacterial silver-doped hydroxyapatite sol coating is performed after the second time coating and sintering process. No change in shape, structure, and mechanical strength occurs after the coating process, drying at 70° C. for 5 hours in still air environment, and heat-treated at 650° C. for 3 hours using a 3-step heat treatment profile (as shown in FIG. 6). When the silver-doped hydroxyapatite sol is coated on a 2 dimensional metallic implant surface, low or minimal bacteria adhesion is observed when compared to the non-coated or non-silver-doped hydroxyapatite coatings: thus, the silver-doped hydroxyapatite sol coating on the 3 dimensional scaffolds of the present invention will similarly provide a strong antibacterial property. Zinc-doped hydroxyapatite sol coating on scaffolds will have the same antibacterial property.

All of the methods disclosed and claimed herein can be made and executed without undue experimentation in light of the present disclosure. While the methods of this invention have been described in terms of preferred embodiments, it will be apparent to those of skill in the art that variations may be applied to the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,629,464
U.S. Pat. No. 5,258,044
U.S. Pat. No. 5,306,305
U.S. Pat. No. 5,543,019
U.S. Pat. No. 5,650,176
U.S. Pat. No. 5,676,976
U.S. Pat. No. 5,683,461
U.S. Pat. No. 5,783,217
U.S. Pat. No. 5,843,289
U.S. Pat. No. 6,027,742
U.S. Pat. No. 6,033,582
U.S. Pat. No. 6,117,456
U.S. Pat. No. 6,132,463
U.S. Pat. No. 6,136,369
U.S. Pat. No. 6,143,948
U.S. Pat. No. 6,171,610
U.S. Pat. No. 6,171,610

U.S. Pat. No. 6,214,368
U.S. Pat. No. 6,309,635
U.S. Pat. No. 6,344,061
U.S. Pat. No. 6,348,069
U.S. Publn. 2002/0037799
U.S. Publn. 2006/0292350
U.S. Publn. 2008/0069852
U.S. Publn. 20080069852
U.S. Publn. 20080075675
U.S. Publn. 20080085292
U.S. Publn. 20080095820
U.S. Publn. 20080095820
U.S. Publn. 20080097618
U.S. Publn. 20080103227
Karageorgiou et al., Biomaterials 26:5474-5491, 2005
Murphy et al., Tissue Engineering 8(1):43-52, 2002.

The invention claimed is:

1. A method of making a bond-like scaffold having a core component and a cortical layer, comprising:
   a) contacting a core polymer porous template and a cortical layer polymer porous template disposed at least partially about the core polymer template with a composition comprising a calcium phosphate, alumina, or zirconia, wherein at least a portion of the core polymer porous template and the cortical layer porous polymer template become coated with the composition; and
   (b) drying the composition coated core polymer porous template and the cortical layer polymer porous template, where a bone-scaffold having a core component and a cortical layer disposed at least partially around the core component is formed.

2. The method of claim 1, wherein the calcium phosphate is tricalcium phosphate, hydroxyapatite, amorphous calcium phosphate, monocalcium phosphate, dicalcium phosphate, octacalcium phosphate, tetracalcium phosphate, fluorapatite, carbonated apatite, an analog thereof, or a mixture thereof.

3. The method of claim 1, wherein the core polymer porous template is at least one of a polyurethane sponge, a polyester sponge, a polyetherketone sponge, and a polypropylene sponge.

4. The method of claim 1, wherein the core polymer porous template is further defined as having about 20 pores per inch (ppi) to about 100 ppi.

5. The method of claim 1, further comprising:
   a) sintering the core polymer porous template and the cortical layer polymer porous template after drying.

6. The method of claim 5, wherein the core component has an average pore diameter of about 100 μm to about 700 μm after sintering, and the cortical layer has an average pore diameter of about 1 μm to about 200 μm after sintering.

7. The method of claim 5, further comprising:
   a) contacting the core component and the cortical layer disposed at least partially about the core component with a composition comprising a calcium phosphate, zirconia, or alumina, wherein at least a majority portion of the core component and the cortical layer become coated with the composition;
   b) drying the composition-coated core component and the cortical layer; and
   c) sintering the core component and cortical layer after drying.

8. The method of claim 1, wherein the method further comprises drilling one or more holes or microchannels through the cortical layer.

9. The method of claim 1, further comprising incorporated a therapeutic agent into the scaffold or applying a therapeutic agent to a surface of the scaffold.

10. The method of claim 9, wherein the therapeutic agent is an angiogenic factor, an osteogenic growth factor, antibiotics, or a biomolecule.

11. The method of claim 1, where the composition initially contacts the core polymer porous template and the cortical layer polymer porous template while the core polymer porous template and the cortical layer polymer porous template is disposed at least partially about the core polymer template.

12. A biomedical scaffold made in accordance with claim 1, comprising:
   a) a core component comprising:
      (i) an open pore structure of micropores that are interconnected; and
      (ii) a hollowed strut comprising microchannels that are interconnected; and
   b) a porous cortical layer in contact with at least a portion of a surface of the core component.

13. The scaffold of claim 12, wherein the cortical layer comprises micropores having an average diameter that is less than the average diameter of the micropores of the core component.

14. The scaffold of claim 12, wherein the micropores have an average diameter of about 100 μm to about 2000 μm, and the microchannels have an average diameter of about 10 μm to about 300 μm.

15. The scaffold of claim 12, wherein the cortical layer comprises micropores having an average diameter of about 1 um to about 2000 um.

16. The scaffold of claim 15, wherein the cortical layer has an average porosity of 30% to 60%.

17. The scaffold of claim 12, wherein the cortical layer comprises microchannels having an average diameter of 1 um to about 2000 um.

18. The scaffold of claim 12, wherein the core component has an average porosity of 65% to 90%.

19. The scaffold of claim 12, wherein the scaffold is comprised of tricalcium phosphate, hydroxyapatite, amorphous calcium phosphate, monocalcium phosphate, dicalcium phosphate, octacalcium phosphate, tetracalcium phosphate, fluorapatite, carbonated apatite, or an analog thereof.

20. The scaffold of claim 12, wherein the core component and/or the cortical layer comprise zinc or silver.

21. A method of treating a tissue defect in a subject, comprising implanting into the bone of a subject a scaffold of claim 12, wherein the tissue defect is treated.

22. The method of claim 21, wherein the subject is a human.

23. The method of claim 21, wherein the tissue defect is a bone defect, a cartilage defect, a tendon defect, or a ligament defect.

24. The method of claim 21, wherein the tissue defect is the result of a bone disease that is fibrous dysplasia, osteoporosis, osteomalacia, arthritis, osteomyelitis, avascular necrosis, Paget's disease, bone cancer, or a traumatic injury.

25. The method of claim 21, further comprising treating the subject with one or more secondary forms of therapy for treatment of a bone defect, bone disease, bone fracture, a cartilage defect, an injury to a ligament, or an injury to a tendon.

26. A kit comprising a scaffold of claim 12 in a sealed container.

27. The scaffold of claim 12, wherein the cortical layer is porous and comprises micropores.

28. The scaffold of claim 27, wherein the cortical layer further comprises microchannels.

29. The scaffold of claim 12, wherein the cortical layer is solid and comprises microchannels.

* * * * *